US008980311B2

(12) United States Patent
Ingale et al.

(10) Patent No.: US 8,980,311 B2

(45) Date of Patent: Mar. 17, 2015

(54) LIPOSOME-MEDIATED LIGATION

(75) Inventors: Sampat Ingale, San Diego, CA (US); Therese Buskas, Athens, GA (US); Geert-Jan Boons, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 809 days.

(21) Appl. No.: 12/315,726

(22) Filed: Dec. 5, 2008

(65) Prior Publication Data

US 2009/0196916 A1 Aug. 6, 2009

Related U.S. Application Data

(63) Continuation-in-part of application No. PCT/US2007/013431, filed on Jun. 7, 2007, which is a continuation-in-part of application No. PCT/US2007/000158, filed on Jan. 3, 2007.

(60) Provisional application No. 60/811,882, filed on Jun. 8, 2006, provisional application No. 60/755,881, filed on Jan. 3, 2006, provisional application No. 60/796,769, filed on May 2, 2006, provisional application No. 60/809,272, filed on May 30, 2006.

(51) Int. Cl.

| | |
|---|---|
| ***A61K 9/127*** | (2006.01) |
| ***A61K 9/50*** | (2006.01) |
| ***B01J 13/02*** | (2006.01) |
| ***B01J 13/04*** | (2006.01) |
| ***C07K 14/47*** | (2006.01) |
| ***A61K 39/00*** | (2006.01) |

(Continued)

(52) U.S. Cl.

CPC .............. *C07K 14/4727* (2013.01); *B01J 13/04* (2013.01); *B01J 13/02* (2013.01); *A61K 39/0011* (2013.01); *A61K 2039/55577* (2013.01); *A61K 2039/6018* (2013.01); *A61K 2039/6087* (2013.01); *C07K 16/2896* (2013.01); *C07K 16/3092* (2013.01); *A61K 38/00* (2013.01); *A61K 39/02* (2013.01); *A61K 39/12* (2013.01); *A61K 39/39* (2013.01); *A61K 2039/57* (2013.01); *C07K 9/00* (2013.01); *C07K 14/22* (2013.01); *C07K 16/3076* (2013.01); *C12N 2770/24234* (2013.01); *G01N 33/5308* (2013.01); *G01N 33/92* (2013.01); *A61K 9/1272* (2013.01)

USPC ............................................ 424/450; 264/4.1

(58) Field of Classification Search

CPC ..... A61K 38/00; A61K 2039/57; A61K 9/50; C12N 277/24234; B01J 13/02; B01J 13/04

USPC ............................................ 424/450; 264/4.1

See application file for complete search history.

(56) References Cited

U.S. PATENT DOCUMENTS

| | | | | |
|---|---|---|---|---|
| 6,310,180 | B1 * | 10/2001 | Tam .............................. | 530/339 |
| 6,413,935 | B1 | 7/2002 | Sette et al. | |

(Continued)

FOREIGN PATENT DOCUMENTS

| | | | |
|---|---|---|---|
| WO | WO 95/07707 A1 | 3/1995 | |
| WO | WO 98/43677 A1 | 10/1998 | |

(Continued)

OTHER PUBLICATIONS

Travassos (EMBO Reports. Sep. 10, 2004 ePub;5(10)1-7).*

(Continued)

*Primary Examiner* — Cherie M Stanfield

(74) *Attorney, Agent, or Firm* — Mueting, Raassch & Gebgardt, P.A.

(57) ABSTRACT

Chemoselective ligation of hydrophobic reactants in a lipid phase.

21 Claims, 13 Drawing Sheets

(51) Int. Cl.

| | |
|---|---|
| ***C07K 16/28*** | (2006.01) |
| ***C07K 16/30*** | (2006.01) |
| ***A61K 39/02*** | (2006.01) |
| ***A61K 39/12*** | (2006.01) |
| ***A61K 39/39*** | (2006.01) |
| ***C07K 9/00*** | (2006.01) |
| ***C07K 14/22*** | (2006.01) |
| ***G01N 33/53*** | (2006.01) |
| ***G01N 33/92*** | (2006.01) |
| *A61K 38/00* | (2006.01) |

(56) References Cited

U.S. PATENT DOCUMENTS

| | | | | |
|---|---|---|---|---|
| 7,482,425 | B2 | 1/2009 | Kochendoerfer et al. | |
| 2002/0038017 | A1 | 3/2002 | Danishefsky et al. | |
| 2002/0055121 | A1 | 5/2002 | Vielkind | |
| 2003/0018169 | A1 * | 1/2003 | Kochendoerfer et al. | 530/350 |
| 2006/0069238 | A1 | 3/2006 | Koganty et al. | |
| 2007/0160622 | A1 | 7/2007 | Turnell et al. | |
| 2009/0041836 | A1 | 2/2009 | Boons et al. | |
| 2009/0246200 | A1 | 10/2009 | Carlson et al. | |

FOREIGN PATENT DOCUMENTS

| | | | |
|---|---|---|---|
| WO | WO 00/12536 | A2 | 3/2000 |
| WO | WO 00/12536 | A3 | 6/2000 |
| WO | WO 03089574 | A2 * | 10/2003 |
| WO | WO 2007/079448 | A2 | 7/2007 |
| WO | WO 2007/146070 | A2 | 12/2007 |
| WO | WO 2007/079448 | A3 | 1/2008 |
| WO | WO 2007/146070 | A3 | 4/2008 |
| WO | WO 2009/035528 | A2 | 3/2009 |
| WO | WO 2010/002478 | A2 | 1/2010 |
| WO | WO 2009/035528 | A3 | 3/2010 |
| WO | WO 2010/002478 | A3 | 7/2010 |

OTHER PUBLICATIONS

Buskas et al., (Angew Chem Int Ed.Sep. 19, 2005;44(37):5985-5988).*

Lemieux et al., (Trends Biotechnol. Dec. 1998;16(12):506-13).*

Ada and Isaacs, "Carbohydrate-protein conjugate vaccines," Feb. 2003 *Clin. Microbiol. Infect.* 9(2):79-85.

Akira et al., "Toll-like receptors: critical proteins linking innate and acquired immunity," Aug. 2001 *Nat. Immunol.*, 2(8):675-680.

Alexander et al., "Development of high potency universal DR-restricted helper epitopes by modification of high affinity DR-blocking peptides," Dec. 1994 *Immunity* 1(9):751-761.

Alexander et al., "Linear PADRE T helper epitope and carbohydrate B cell epitope conjugates induce specific high titer IgG antibody responses," Feb. 1, 2000 *J. Immunol.* 164(3):1625-1633.

Alexandrov et al., "Intein-mediated synthesis of geranylgeranylated Rab7 protein in vitro," May 22, 2002 *J. Am. Chem. Soc.* 124(20):5648-5649.

Baldus et al., "MUC1 and the MUCs: a family of human mucins with impact in cancer biology," 2004 *Crit. Rev. Clin. Lab. Sci.* 41(2):189-231.

Bang et al., "Total chemical synthesis of crambin," Feb. 11, 2004 *J. Am. Chem. Soc.* 126(5):1377-1383. Available online on Jan. 20, 2004.

Barber and Fayrer-Hosken, "Possible mechanisms of mammalian immunocontraception," Mar. 2000 *J. Reprod. Immunol.* 46(2):103-124.

Becker et al., "Total chemical synthesis of a functional interacting protein pair: the protooncogene H-Ras and the Ras-binding domain of its effector c-Raf1," Apr. 29, 2003 *PNAS* 100(9):5075-5080. Available online on Apr. 18, 2003.

BenMohamed et al., "Lipopeptide vaccines—yesterday, today, and tomorrow," Jul. 2002 *Lancet Infect. Dis.* 2(7):425-431.

Blander and Medzhitov, "Toll-dependent selection of microbial antigens for presentation by dendritic cells," Apr. 6, 2006 *Nature* 440(7085):808-812. Available online on Feb. 19, 2006.

Boons, Geert-Jan, "Synthesis/Immunological Properties of Lewis Antigens," Grant Abstract, Grant No. 1RO1CA088986-01A2 [online]. National Cancer Institute, National Institutes of Health; project dates Jul. 15, 2002 to Jun. 30, 2006 [retrieved on Jan. 6, 2009]. Retrieved from the Internet: <http://crisp.cit.nih.gov/crisp/CRISP_LIB.getdoc?textkey=6546986&p_grant_num=1R01CA088986-01A2&p_query=&ticket=84444686&p_audit_session_id=393574951&p_keywords=>; 2 pgs.

Boons, Geert-Jan, "Synthesis/Immunological Properties of Lewis Antigens," Grant Abstract, Grant No. 5RO1CA088986-02 [online]. National Cancer Institute, National Institutes of Health; project dates Jul. 15, 2002 to Jun. 30, 2006 [retrieved on Jan. 6, 2009]. Retrieved from the Internet: <http://crisp.cit.nih.gov/crisp/CRISP_LIB.getdoc?textkey=6605801&p_grant num=5R01CA088986-02&p_query=&ticket=8-4444686&p_audit_session_id=3935749-51&p_keywords=>; 2 pgs.

Boons, Geert-Jan, "Synthesis/Immunological Properties of Lewis Antigens," Grant Abstract, Grant No. 5RO1CA088986-03 [online]. National Cancer Institute, National Institutes of Health; project dates Jul. 15, 2002 to Jun. 30, 2006 [retrieved on Jan. 6, 2009]. Retrieved from the Internet: <http://crisp.cit.nih.gov/crisp/CRISP_LIB.getdoc?textkey=6752388&p_grant_num=5R01CA088986-03&p_query=&ticket=4444686&p_audit_session_id=393574951&p_keywords=>; 2 pgs.

Boons, Geert-Jan, "Synthesis/Immunological Properties of Lewis Antigens," Grant Abstract, Grant No. 5RO1CA088986-04 [online]. National Cancer Institute, National Institutes of Health; project dates Jul. 15, 2002 to Nov. 30, 2006 [retrieved on Jan. 6, 2009]. Retrieved from the Internet: <http://crisp.cit.nih.gov/crisp/CRISP_LIB.getdoc?textkey=6918562&p_grant_num=5R01CA088986-04&p_query=&ticket=84444686&p_audit_session_id=393574951&p_key words=>; 2 pgs.

Boons, Geert-Jan, "A Fully Synthetic Carbohydrate-Based Cancer Vaccine," Grant Abstract, Grant No. 2RO1CA088986-05 [online]. National Cancer Institute, National Institutes of Health; project dates Jul. 15, 2002 to Nov. 30, 2010 [retrieved on Jan. 6, 2009]. Retrieved from the Internet: <http://crisp.cit.nih.gov/crisp/CRISP_LIB.getdoc?textkey=7212472&p_grant_num=2R01CA088986-05&p_query=&ticket=8-4444686&p_audit_session_id=3935749-51& p_key words=>; 2 pgs.

Boons, Geert-Jan, "A Fully Synthetic Carbohydrate-Based Cancer Vaccine," Grant Abstract, Grant No. 5RO1CA088986-06 [online]. National Cancer Institute, National Institutes of Health; project dates Jul. 15, 2002 to Nov. 30, 2010 [retrieved on Jan. 6, 2009]. Retrieved from the Internet: <http://crisp.cit.nih.gov/crisp/CRISP_LIB.getdoc?textkey=7329834&p_grant_num=5R01CA088986-06&p_query=&ticket=8-4444686&p_audit_session_id=393574951 &p_keywords=>; 1 pg.

Boons, Geert-Jan, "A Fully Synthetic Carbohydrate-Based Cancer Vaccine," Grant Abstract, Grant No. 5RO1CA088986-07 [online]. National Cancer Institute, National Institutes of Health; project dates Jul. 15, 2002 to Nov. 30, 2010 [retrieved on Jan. 6, 2009]. Retrieved from the Internet: <http://crisp.cit.nih.gov/crisp/CRISP_LIB.getdoc?textkey=7534051&p_grant_num=5R01CA088986-07&p_query=&ticket=84444686&p_audit_session_id=393574951&p_keywords=>; 1 pg.

Bräse et al., "Organic azides: an exploding diversity of a unique class of compounds," Aug. 19, 2005 *Angew Chem. Int. Ed.* 44(33):5188-5240.

Braun, "Covalent lipoprotein from the outer membrane of *Escherichia coli*," Oct. 31, 1975 *Biochim. Biophys. Acta* 415(3):335-377.

Buskas et al., "Towards a fully synthetic carbohydrate-based anticancer vaccine: synthesis and immunological evaluation of a lipidated glycopeptide containing the tumor-associated Tn antigen," Sep. 19, 2005 *Angew. Chem.* 117(37):6139-6142. Available online on Aug. 18, 2005. Also published concurrently in *Angew. Chem. Int. Ed.* 44(37):5985-5988.

(56) References Cited

OTHER PUBLICATIONS

Buskas et al., "Glycopeptides as versatile tools for glycobiology," Aug. 2006 *Glycobiology* 16(8):113R-136R. Available online on May 4, 2006.
Caroff et al., "Structural and functional analyses of bacterial lipopolysaccharides," Jul. 2002 Microbes Infect. 4(9):915-926.
Cato et al., "Highly efficient stereospecific preparation of Tn and TF building blocks using thioglycosyl donors and the $Ph_2SO/Tf_2O$ promoter system," Aug. 2005 *J. Carb. Chem.* 24 (4-6):503-516.
Clayton et al., "Total chemical synthesis and electrophysiological characterization of mechanosensitive channels from *Escherichia coli* and *Mycobacterium tuburculosis*," Apr. 6, 2004 *PNAS* 101(14):4764-4769. Available online on Mar. 23, 2004.
Croce and Segal-Eiras, "The use of carbohydrate antigens for the preparation of vaccines for therapy in breast cancer," Nov. 2002 *Drugs Today* 38(11):759-768.
Danishefsky and Allen, "From the laboratory to the clinic: a retrospective on fully synthetic carbohydrate-based anticancer vaccines," Mar. 2000 *Angew Chem. Int. Ed.* 39(5):836-863.
Dawson et al., "Synthesis of proteins by native chemical ligation," Nov. 4, 1994 *Science* 266(5186):776-779.
Dawson et al., "Modulation of reactivity in native chemical ligation through the use of thiol additives," May 14, 1997 *J. Am. Chem. Soc.* 119(19):4325-4329.
Dawson and Kent, "Synthesis of native proteins by chemical ligation," Jul. 2000 *Ann. Rev. Biochem.* 69:923-960.
DeFranco, "B-cell activation 2000," Aug. 2000 *Immunol. Rev.* 176:5-9.
Diekman et al., "Evidence for a unique N-linked glycan associated with human infertility on sperm CD52: a candidate contraceptive vaccinogen," Oct. 1999 *Immunol. Rev.* 171:203-211.
Dixon and Darveau, "Lipopolysaccharide heterogeneity: innate host responses to bacterial modification of lipid A structure," Jul. 2005 *J. Dent. Res.* 84(7):584-595.
Doores et al., "Exploring and exploiting the therapeutic potential of glycogonjugates," Jan. 11, 2006 *Chem. Eur. J.* 12(3):656-665. Available online on Sep. 27, 2005.
Dube and Bertozzi, "Glycans in cancer and inflammation—potential for therapeutics and diagnostics," Jun. 2005 *Nat. Rev. Drug Disc.* 4(6):477-488.
Dziadek et al., "Synthetic vaccines consisting of tumor-associate MUC1 glycopeptide antigens and bovine serum albumin," Nov. 25, 2005 *Angew. Chem. Int. Ed.* 44(46):7624-7630. Available online on Oct. 25, 2005.
Espuelas et al., "Effect of synthetic lipopeptides formulated in liposomes on the maturation of human dendritic cells," Apr. 2005 *Mol. Immunol.* 42(6):721-729. Available online on Nov. 11, 2004.
Fearon and Carroll, "Regulation of B lymphocyte responses to foreign and self-antigens by the CD19/CD21 complex," 2000 *Ann. Rev. Immunol.* 18:393-422.
Fox et al., "Carbohydrates and glycoproteins of *Bacillus anthracis* and related bacilli: targets for biodetection," Aug. 2003 *J. Microbiol. Meth.* 54(2):143-152.
Foy et al., "Immune regulation by CD40 and its ligand GP39," 1996 *Ann. Rev. Immunol.* 14:591-617.
Fujita et al., "Investigation toward multi-epitope vaccine candidates using native chemical ligation," 2008 *Biopolymers* (*Peptide Sci.*) 90(5):624-632. Available online on Apr. 21, 2008.
Gibbons et al., "Lipidic peptides, I. Synthesis, resolution and structural elucidation of lipidic amino acids and their homo- and hetero-oligomers," 1990 *Liebigs Ann. Chem.* 1990(2):1175-1183.
Goffard et al., "Role of N-linked glycans in the functions of Hepatitis C virus envelope glycoproteins," Jul. 2005 *J. Virol.* 79(13):8400-8409.
Goldblatt, "Recent developments in bacterial conjugate vaccines," Jul. 1998 *J. Med. Microbiol.* 47(7):563-567.
Grogan et al., "Synthesis of lipidated green fluorescent protein and its incorporation in supported lipid bilayers," Oct. 19, 2005 *J. Am. Chem. Soc.* 127(41):14383-14387.
Guo and Shao, "Glycopeptide and glycoprotein synthesis involving unprotected carbohydrate building blocks," Nov. 2005 *Med. Res. Rev.* 25(6):655-678. Available online on May 13, 2005.
Hakomori and Zhang, "Glycosphingolipid antigens and cancer therapy," Feb. 1997 *Chem. Biol.* 4(2):97-104.
Hakomori, "Cancer-associated glycosphingolipid antigens: their structure, organization, and function," 1998 *Acta Anat.* 161(1-4):79-90.
Harris et al., "Synthesis of a C-terminal thioester derivative of the lipopeptide $Pam_2CSKKKKG$ using Fmoc SPSS," 2007 *Syn. Lett.* 5:713-716. Available online on Aug. 3, 2007.
Hayakawa and Hardy, "Development and function of B-1 cells," Jun. 2000 *Curr. Opin. Immunol.* 12(3):346-353.
Hermanson (ed), *Bioconjugate Techniques* Academic Press: San Diego, CA. 1996 Cover page, publishers page, and table of contents (15 pgs).
Huisgen, "1,3-dipolar cycloadditions: Introduction, Survey, Mechanism," pp. 1-177 in Padwa (Ed), *1,3-Dipolar cycloaddition chemistry* (*vol. 1*). John Wiley & Sons: New York, NY; 1984. Cover page, publishers page, and table of contents (3 pgs).
Hunter and Kochendoerfer, "Native chemical ligation of hydrophobic peptides in lipid bilayer systems," May/Jun. 2004 *Bioconj. Chem.* 15(3):437-440. Available online on Apr. 24, 2004.
Ingale et al., "Synthesis of glyco(lipo)peptides by liposome-mediated native chemical ligation," Dec. 7, 2006 *Org. Lett.* 8(25):5785-5788. Available online on Nov. 16, 2006.
Ingale et al., Supplemental Information for "Synthesis of glyco(lipo)peptides by liposome-mediated native chemical ligation," Dec. 7, 2006 *Org. Lett.* 8(25):5785-5788. Available online at <http://pubs.acs.org/subscribe/journals/orlef7/suppinfo/o1062423x/o1062423xsi20061107_021934.pdf>; 32 pages.
Ingale et al., "Robust immune responses elicited by a fully synthetic three-component vaccine," 2007 *Nat. Chem. Biol.* 3(10):663-667. Available online on Sep. 2, 2007.
Ingenito et al., "Solid phase synthesis of peptide C-terminal thioesters by Fmoc/*t*-Bu chemistry," Dec. 15, 1999 *J. Am. Chem. Soc.* 121(49):11369-11374. Available online on Nov. 25, 1999.
International Preliminary Report on Patentability issued in International Application PCT/US2007/000158 on Jul. 8, 2008.
International Preliminary Report on Patentability issued in International Application PCT/US2007/013431 on Dec. 10, 2008.
International Search Report issued in International Application PCT/US2009/003944 on May 3, 2010.
Jackson et al., "A totally synthetic vaccine of generic structure that targets Toll-like receptor 2 on dendritic cells and promotes antibody or cytotoxic T cell responses," Oct. 26, 2004 *PNAS* 101(43):15440-15445. Available online on Oct. 15, 2004.
Jones, "Vaccines based on the cell surface carbohydrates of pathogenic bacteria," Jun. 2005 *Anais da Acad. Brasilia de Ciencias* 77(2):293-324. Available online on May 9, 2005.
Kagan et al., "Comparison of antigen constructs and carrier molecules for augmenting the immunogenicity of the monosaccharide epithelial cancer antigen Tn," May 2005 *Cancer Immunol. Immunother.* 54(5):424-430. Available online on Dec. 30, 2004.
Kenner et al., "The safety catch principle in solid phase peptide synthesis," 1971 *Chemical Communications* 12:636-637.
Knorr et al., "New coupling reagents in peptide chemistry," 1989 *Tetrahedron Lett.* 30(15):1927-1930.
Kochendoerfer et al., "Design and chemical synthesis of a homogeneous polymer-modified erythropoiesis protein," Feb. 7, 2003 *Science* 299(5608):884-887.
Köhn and Breinbauer, "The Staudinger ligation—a gift to chemical biology," Jun. 14, 2004 *Angew. Chem. Int. Ed.* 43(24):3106-3116. Available online on May 12, 2004.
Kolb et al., "Click chemistry: diverse chemical function from a few good reactions," Jun. 1, 2001 *Agnew Chem. Int. Ed.* 40(11):2004-2021.
Koppel et al., "Distinct functions of DC-SIGN and its homologues L-SIGN (DC-SIGNR) and mSIGNR1 in pathogen recognition and immune regulation," Feb. 2005 *Cell. Microbiol.* 7(2):157-165.
Koppitz et al., "Synthesis of unnatural lipophilic *N*-(9*H*-Fluoren-9-ylmethoxy)carbonyl-substituted α-amino acids and their incorpora-

(56) References Cited

OTHER PUBLICATIONS tion into cyclic RGD-peptides: a structure-activity study," Jun. 30, 1997 *Helv. Chim. Acta* 80(4):1280-1300.
Kuberan and Linhardt, "Carbohydrate based vaccines," 2000 *Curr. Org. Chem.* 4(6):653-677.
Kuduk et al., "Synthetic and immunological studies on clustered modes of mucin-related Tn and TF O-linked antigens: the preparation of a glycopeptide-based vaccine for clinical trials against prostate cancer," Dec. 9, 1998 *J. Am. Chem. Soc.* 120(48):12474-12485. Available online on Nov. 20, 1998.
Kurosaki, "Regulation of B-cell signal transduction by adaptor proteins," May 2002 *Nat. Rev. Immunol.* 2(5):354-363.
Macmillan and Bertozzi, "Modular assembly of glycoproteins: towards the synthesis of GlyCAM-1 by using expressed protein ligation," Mar. 5, 2004 *Angew. Chem. Int. Ed.* 43(11):1355-1359.
Medzhitov and Janeway, Jr., "Innate immunity: impact on the adaptive immune response," Feb. 1997 *Curr. Opin. Immunol.* 9(1):4-9.
Mendonca-Previato et al., "Protzoan parasite-specific carbohydrate structures," Oct. 2005 *Curr. Opin. Struct. Biol.* 15(5):499-505. Available online on Sep. 8, 2005.
Mergler et al., "The aspartimide problem in Fmoc-based SPPS. Part II," Aug. 2003 *J. Pept. Sci.* 9(8):518-526.
Metzger et al., "Lipopeptides containing 2-(palmitoylamino)-6,7-bis(palmitoyloxy) heptanoic acid: synthesis, stereospecific stimulation of B-lymphocytes and macrophages, and adjuvanticity in vivo and in vitro," Jul. 1991 *J. Med. Chem.* 34(7):1969-1974.
Nyame et al., "Antigenic glycans in parasitic infections: implications for vaccines and diagnostics," Jun. 15, 2004 *Arch. Biochem. Biophys.* 426(2):182-200.
Otaka et al., "Facile synthesis of membrane-embedded peptides utilizing lipid-bilayer-assisted chemical ligation," Aug. 7, 2004 *Chem. Comm.* 1722-1723. Available online on Jun. 28, 2004.
Ouerfelli et al., "Synthetic carbohydrate-based antitumor vaccines: challenges and opportunities," Oct. 2005 *Exp. Rev. Vaccines* 4(5):677-685.
Ozawa et al., "Efficient sequential segment coupling using N-alkylcysteine-assisted thioesterification for glycopeptide dendrimer synthesis," 2008 *Org. Lett.* 10(16):3531-3533. Available online on Jul. 19, 2008.
Pier, "Application of vaccine technology to prevention of *Pseudomonas aeruginosa* infections," Oct. 2005 *Exp. Rev. Vaccines* 4(5):645-656.
Raetz and Whitfield, "Lipopolysaccharide endotoxins," 2002 *Ann. Rev. Biochem.* 71:635-700. Available online on Apr. 30, 2002.
Roach et al., "The evolution of vertebrate Toll-like receptors," Jul. 5, 2005 *PNAS* 102(27):9577-9582. Available online on Jun. 23, 2005.
Roth et al., "Synthesis of thiol-reactive lipopeptide adjuvants. Incorporation into liposomes and study of their mitogenic effect on mouse splenocytes," May-Jun. 2004 *Bioconj. Chem.* 15(3):541-553. Available online on May 1, 2004.
Shin et al., "Fmoc-based synthesis of peptide-$\alpha$thioesters: application to the total chemcial synthesis of a glycoprotein by native chemical ligation," Dec. 22, 1999 *J. Am. Chem. Soc.* 121(50):11684-11689. Available online on Dec. 7, 1999.
Snijdewint et al., "Antibody-dependent cell-mediated cytotoxicity can be induced by MUC1 peptide vaccination of breast cancer patients," Jul. 1, 2001 *Int. J. Cancer* 93(1):97-106.
Sørenson, "Neutralization epitopes on HIV pseudotypes with HTLV-I," Dec. 1996 *Persp. Drug Disc. Design* 5(1):154-160.
Spohn et al., "Synthetic lipopeptide adjuvants and Toll-like receptor 2-structure-activity relationships," Jun. 23, 2004 *Vaccine* 22(19):2494-2499. Available online on Apr. 8, 2004.
Springer, "T and Tn, general carcinoma autoantigens," Jun. 15, 1984 *Science* 224(4654):1198-1206.
Springer, "Immunoreactive T and Tn epitopes in cancer diagnosis, prognosis, and immunotherapy," Aug. 1997 *J. Mol. Med.* 75(8):594-602.
Tam, "Recent advances in multiple antigen peptides," Sep. 13, 1996 *J. Immunol. Meth.* 196(1):17-32.
Toyokuni et al., "Synthetic vaccines: synthesis of a dimeric Tn antigen-lipopeptide conjugate that elicits immune responses against Tn-expressing glycoproteins," Jan. 1994 *J. Am. Chem. Soc.* 116(1):395-396.
Valiyaveetil et al., "Semisynthesis and folding of the potassium channel KcsA," Aug. 7, 2002 *J. Am. Chem. Soc.* 124(31):9113-9120. Available online on Jul. 11, 2002.
van Duin et al., "Triggering TLR signaling in vaccination," Jan. 2006 *TRENDS Immunol.* 27(1)::49-55. Available online on Nov. 23, 2005.
Veber et al., "Acetamidomethyl. A novel thiol protecting group for cysteine," Jul. 26, 1972 *J. Am. Chem. Soc.* 94(15):5456-5461.
Vliegenthart, "Carbohydrate based vaccines," May 22, 2006 *FEBS Lett.* 580(12):2945-2950. Available online on Mar. 29, 2006.
Wang, "Toward oligosaccharide- and glycopeptide-based HIV vaccines," Mar. 2006 *Curr. Opin. Drug Disc. Dev.* 9(2):194-206.
Warren et al., "Synthetic glycopeptide-based vaccines," 2007 *Top. Curr. Chem.* 267:109-141. Available online on Mar. 9, 2006.
Westerlind et al., "Synthetic vaccines consisting of tumor-associated MUC1 glycopeptide antigens and a T-cell epitope for the induction of a highly specific humoral immune response," 2008 *Angew. Chem. Int. Ed.* 47:7551-7556. Available online on Aug. 14, 2008.
Wiertz et al., "Identification of T cell epitopes occurring in a meningococcal class 1 outer membrane protein using overlapping peptides assembled with simultaneous multiple peptide synthesis," Jul. 1, 1992 *J. Exp. Med.* 176(1):79-88.
Wiessmüller et al., "Peptide vaccines and peptide libraries," Apr. 2001 *Biol. Chem.* 382(4):571-579.
Written Opinion issued in International Application PCT/US2007/000158 on Jul. 3, 2008.
Written Opinion issued in International Application PCT/US2007/013431 on Feb. 29, 2008.
Written Opinion issued in International Application PCT/US2009/003944 on May 3, 2010.
Yang et al., "Sugar-assisted ligation in glycoprotein synthesis," 2007 *JACS* 129:7690-7701. Available online on May 25, 2007.
Yeo et al., "Expanded utility of the native chemical ligation reaction," Oct. 4, 2004 *Chem. Eur. J.* 10(19):4664-4672. Available online on Aug. 11, 2004.
Akintonwa, "Theoretical mechanistic basis of the toxic effects and efficacy of dideoxycytidine in HIV:AIDS," Aug. 2001 *Medical Hypotheses* 57:249-251.
Comer et al., "Characterization of a mouse monoclonal antibody specific for O-linked N-acetylglucomasmine," 2001 *Anal. Biochem.* 293:169-177.
Devine et al., "The breast tumor-associate epitope defined by monoclonal antibody 3E1.2 is an O-linked mucin carbohydrate containing N-glycoylyneuraminic acid," Nov. 1, 1991 *Cancer Res.* 51:5826-5836.
Dudkin et al., "Toward fully synthetic carbohydrate-based HIV antigen design: on the critical role of bivalency," Aug. 11, 2004 *J. Am. Chem. Soc.* 126:9560-9562.
Ingale et al., "Synthesis of glycolipopeptide as vaccine against cancer," Poster Abstract [online]. Abstract No. CARB 81, Division of Carbohydrate Chemistry. 229th *American Chemical Society (ACS) National Meeting*. San Diego, CA; Mar. 13-17, 2005. Available online [retrieved on Jan. 6, 2009]. Retrieved from the Internet: oasys2.confex.com/acs/229nm/techprogram/P839449.HTM>; 1 pg.
International Preliminary Report on Patentability issued Jan. 5, 2011, International Patent Application No. PCT/US2009/003944, filed Jul. 2, 2009.
Kudryashov et al., "Toward optimized carbohydrate-based anticancer vaccines: epitope clustering, carrier structure, and adjuvant all influence antibody responses to Lewis[y] conjugates in mice," Mar. 13, 2001 *Proc. Natl. Acad. Sci. U.S.A.* 98(6):3264-3269.
Nozawa et al., "HMMC-1: a humanized monoclonal antibody with therapeutic potential against Müllerian duct-related carcinomas," Oct. 15, 2004 *Clin. Cancer Res.* 10:7071-7178.
Office Action issued Mar. 8, 2010, in U.S. Appl. No. 12/217,376.
Op de Beck et al., "Biogenesis of hepatitis C virus envelope glycoproteins," Nov. 2001 *J. Gen. Virol.* 82:2589-2595.
Reichel et al., "Synthetic carbohydrate-based vaccines: synthesis of an L-*glycero*-D-*manno*-heptose antigen-T-epitope-lipopeptide conjugate," 1997 *Chem. Commun.* 21:2087-2088.
van Kuppevelt et al., "Generation and application of type-specific anti-heparan sulfate antibodies using phage display technology," May 22, 1998 *J. Biol. Chem.* 273:12960-12966.

\* cited by examiner

1

Scheme 1. Synthesis of three-component vaccine by NCL

Scheme 2. Preparation of 10 from 5 and 8

Scheme 3. Preparation of 11 and 12 from 3, 6, 8, and 9

15 Rink amide resin

16

17

18

19

20, R = OAc

3, R = H

Scheme 4. Synthesis of the Cys-glycopeptide 3

21

22

23

24

2

Scheme 5. Synthesis of Cys(Acm)-thioester peptide 2.

21
25
29
30
6

Scheme 6. Chemical synthesis of lipopeptide thioester 6

21 32 33 31 8

Scheme 7. Chemical synthesis of lipidated amino acid thioester 8

Scheme 8. Sequential native chemical ligation of 7 or 10

21

34

35

36

9

Scheme 9. Cys (Acm)-T-epitope thioester 9

9

3

11 or

12

Scheme 10. Sequential native chemical ligation of 11 or 12

39

38

37

Scheme 11. Liposome-mediated native chemical ligation of glycolipopeptide 37 in the absence of thiol initiator

SEQUENCE LISTING

<160> NUMBER OF SEQ ID NOS: 8

<210> SEQ ID NO 1

-continued

```
<211> LENGTH: 15
<212> TYPE: PRT
<213> ORGANISM: Clostridium tetani

<400> SEQUENCE: 1

Gln Tyr Ile Lys Ala Asn Ser Lys Phe Ile Gly Ile Thr Glu Leu
1               5                   10                  15


<210> SEQ ID NO 2
<211> LENGTH: 20
<212> TYPE: PRT
<213> ORGANISM: Neisseria meningitidis

<400> SEQUENCE: 2

Tyr Ala Phe Lys Tyr Ala Arg His Ala Asn Val Gly Arg Asn Ala Phe
1               5                   10                  15

Glu Leu Phe Leu
            20


<210> SEQ ID NO 3
<211> LENGTH: 13
<212> TYPE: PRT
<213> ORGANISM: Human poliovirus 1

<400> SEQUENCE: 3

Lys Leu Phe Ala Val Trp Lys Ile Thr Tyr Lys Asp Thr
1               5                   10


<210> SEQ ID NO 4
<211> LENGTH: 15
<212> TYPE: PRT
<213> ORGANISM: Clostridium tetani

<400> SEQUENCE: 4

Val Ser Ile Asp Lys Phe Arg Ile Phe Cys Lys Ala Asn Pro Lys
1               5                   10                  15


<210> SEQ ID NO 5
<211> LENGTH: 16
<212> TYPE: PRT
<213> ORGANISM: Clostridium tetani

<400> SEQUENCE: 5

Leu Lys Phe Ile Ile Lys Arg Tyr Thr Pro Asn Asn Glu Ile Asp Ser
1               5                   10                  15


<210> SEQ ID NO 6
<211> LENGTH: 16
<212> TYPE: PRT
<213> ORGANISM: Clostridium tetani

<400> SEQUENCE: 6

Ile Arg Glu Asp Asn Asn Ile Thr Leu Lys Leu Asp Arg Cys Asn Asn
1               5                   10                  15


<210> SEQ ID NO 7
<211> LENGTH: 21
<212> TYPE: PRT
<213> ORGANISM: Clostridium tetani

<400> SEQUENCE: 7

Phe Asn Asn Phe Thr Val Ser Phe Trp Leu Arg Val Pro Lys Val Ser
1               5                   10                  15

Ala Ser His Leu Glu
```

-continued

```
            20


<210> SEQ ID NO 8
<211> LENGTH: 18
<212> TYPE: PRT
<213> ORGANISM: Plasmodium falciparum

<400> SEQUENCE: 8

Glu Lys Lys Ile Ala Lys Met Glu Lys Ala Ser Ser Val Phe Asn Val
1               5                   10                  15

Asn Asn
```

LIPOSOME-MEDIATED LIGATION

This application is a continuation-in-part of International Application No. PCT/US2007/013431, filed Jun. 7, 2007, which claims the benefit of U.S. Provisional Application Ser. No. 60/811,882, filed Jun. 8, 2006; further, International Application No. PCT/US2007/013431 is a continuation-in-part of International Application No. PCT/US2007/000158, filed Jan. 3, 2007, which claims the benefit of U.S. Provisional Application Ser. No. 60/755,881, filed Jan. 3, 2006, U.S. Provisional Application Ser. No. 60/796,769, filed May 2, 2006, and U.S. Provisional Application Ser. No. 60/809,272, filed May 30, 2006; all of which are incorporated herein by reference in their entireties.

STATEMENT OF GOVERNMENT RIGHTS

This invention was made with government support under a grant from the National Cancer Institute of the National Institutes of Health, Grant No. RO1CA088986. The U.S. Government has certain rights in this invention.

BACKGROUND OF THE INVENTION

Native chemical ligation (NCL) is a chemo-selective reaction that occurs at physiological pH between an N-terminal cysteine residue and a C-terminal peptide thioester (Dawson et al., Science 1994, 266, 776-779; Dawson et al., Annu. Rev. Biochem. 2000, 69, 923-960; Yeo et al., Chem.-Eur. J. 2004, 10, 4664-4672). In the first step of ligation, a reversible trans-thioesterification takes place between the C-terminal thioester and the sulfhydryl group from the N-terminal cysteine residue. The ligated peptide thioester then undergoes a rapid, irreversible and spontaneous intramolecular S→N shift, generating the thermodynamically favored native amide bond at the ligation junction. NCL occurs uniquely at an N-terminal cysteine residue regardless of the presence of any additional internal cysteine residues and, as this ligation method is compatible with both carbohydrates and peptides, provides access to glycopeptides.

The applicability of NCL is reduced when peptide segments are poorly soluble in aqueous buffer. Since NCL is usually performed in aqueous buffers, this can present complications when one of the reactants to be ligated has hydrophobic character. Recently, some researchers have attempted to use native chemical ligation to link selected reactants to membrane-spanning domain fragments of transmembrane proteins. Otaka et al. covalently linked two membrane-embedded transmembrane peptide domains at a ligation site that was situated in the hydrophilic extracellular loop region (Chem Commun., 2004, 1722-1723). Hunter et al. attached a small soluble peptide to the end of a transmembrane peptide embedded in a cubic lipidic phase matrix (Bioconjugate Chem., 2004, 15:437; U.S. Pat. Publ. 20030018169, published Jan. 23, 2003).

There remains, however, a need for reliable processes for chemical ligation of a wide variety of hydrophobic molecules including compounds that contain lipid and/or carbohydrate moieties.

SUMMARY OF THE INVENTION

The invention provides a method for chemoselective ligation, more particularly native chemical ligation (NCL), of hydrophobic reactants in a lipid phase to produce a multicomponent ligation product. The reactants are embedded or solubilized within a lipidic structure such as a lipid monolayer, lipid bilayer, a liposome, a micelle, a film, an emulsion, matrix, or a gel. The lipid structure is typically formed from nonpolar, hydrophobic and/or amphipathic components, such as phospholipids. Preferably, the thioester and cysteine moieties that are involved in the chemoselective native chemical ligation reaction are positioned within the lipid phase such that the ligation reaction takes place within the lipidic structure.

In one embodiment of the method of the invention, one or more first and second hydrophobic reactants are initially mixed with one or more lipid phase components. In a preferred embodiment, the first hydrophobic reactant includes an N-terminal cysteine residue, and the second hydrophobic reactant includes a thioester. The lipid phase components are nonpolar, hydrophobic and/or amphipathic molecules that are capable of forming a lipidic structure. The mixture is subjected to conditions effective to form a lipidic structure in which the first and second reactants are embedded. The first and second reactants are then subjected to conditions effective to allow ligation of the first reactant and the second reactant to yield a multicomponent compound comprising the first and second reactant. Optionally, one or both of the first and second reactants is not a transmembrane protein or membrane-spanning fragment thereof.

Another embodiment of the method of the invention utilizes a preformed lipidic structure. The first and second hydrophobic reactants are contacted with a preformed lipidic structure under conditions to allow ligation of the first reactant and the second reactant to yield a multicomponent compound comprising the first and second reactant.

The method of the invention optionally further includes contacting the resulting (first) multicomponent compound with at least one third hydrophobic reactant within a lipid structure under conditions to allow ligation of the multicomponent compound and the third reactant, to yield a second, further multicomponent compound comprising the first, second and third reactants. Preferably, prior to or concurrent with ligation, the first multicomponent compound and the third reactant are solubilized within a lipidic structure to facilitate ligation of the first multicomponent to the third reactant.

Preferably, the linkage reaction takes place in the lipid phase, within the lipidic structure, rather than at the interface between the lipidic structure and the external aqueous environment.

The use of an initiator compound, such as a thiol, to catalyze the ligation is optional. The ligation is readily performed in the absence of an initiator compound.

Optionally, in any method of the invention, one or more of the first, second or third hydrophobic reactants are not transmembrane proteins or membrane-spanning fragments thereof.

One example of a compound that can be produced by the method of the invention is a multicomponent vaccine. The reactants used in the ligation reaction can, for example, take the form of vaccine components such as a carbohydrate component, a peptide component, a lipid component, or conjugates or combinations thereof. A multicomponent vaccine can be synthesized, for example, from lipopeptide thioester, peptide and glycopeptide reactants (FIG. 2) using the method of the invention. These reactants can be advantageously designed or selected to include desired antigenic or immunogenic features, such as T-epitopes or B-epitopes. A reactant that includes a T-epitope may be, for example, a peptide, glycopeptide, or lipopeptide. A reactant that includes a B-epitope may be, for example, a carbohydrate-containing compound. The B-epitope can be from a microorganism such as a virus, e.g., human immunodeficiency virus or hepatitis C virus, or from a bacterium, a fungus, or a protozoan. The B-epitope can be one that is overexpressed on a cancer cell. The carbohydrate may be a self-antigen, such as a MUC-1 glycopeptide. A carbohydrate reactant useful in vaccine synthesis can include a glycoconjugate selected from the group consisting of a glycosylated protein, a glycosylated peptide, a glycosylated lipid, a glycosylated amino acid, a DNA and an RNA. A lipid reactant useful in vaccine synthesis can, for example, include a lipopeptide adjuvant. One example of a suitable lipid reactant is a compound that includes a Toll-like receptor (TLR) ligand, such as $Pam_3Cys$ or $Pam_3CysSK_n$, wherein n=0, 1, 2, 3, 4 or 5, preferably $Pam_3CysSK_4$.

Unless otherwise specified, “a,” “an,” “the,” and “at least one” are used interchangeably and mean one or more than one.

Abbreviations: Cha, cyclohexylalanine; DIPEA, N,N-diisopropylethylamine; DMF, dimethylformamide; DPC, dodecylphosphocholine; DTT, dithiothreitol; EDT, 1,2-ethanedithiol; EDTA, ethylenediaminetetraacetic acid; Fmoc, fluorenylmethoxycarbonyl; HATU, O-(7-azabenzotriazol-1-yl)-N,N,N',N'-tetramethyl-uronium hexafluorophosphate; HBTU, 2-(1H-benzotriazole-1-yl)-1,3,3,3-tetramethylaminium hexafluorophosphate; HOAt, 1-hydroxy-7-azabenzotriazole; HOBt, N-hydroxybenzotriazole; NCL, native chemical ligation; NMP, N-methylpyrrolidone; PyBOP, benzotriazole-1-yl-oxy-tris-pyrrolidino-phosphonium hexafluorophosphate; SPPS, solid phase peptide synthesis; TCEP, Tris[2-carboxyethyl]phosphine; TFA, trifluoroacetic acid; THF, tetrahydrofuran; TIS, triisopropylsilane.

DETAILED DESCRIPTION OF ILLUSTRATIVE EMBODIMENTS

Figure 1:
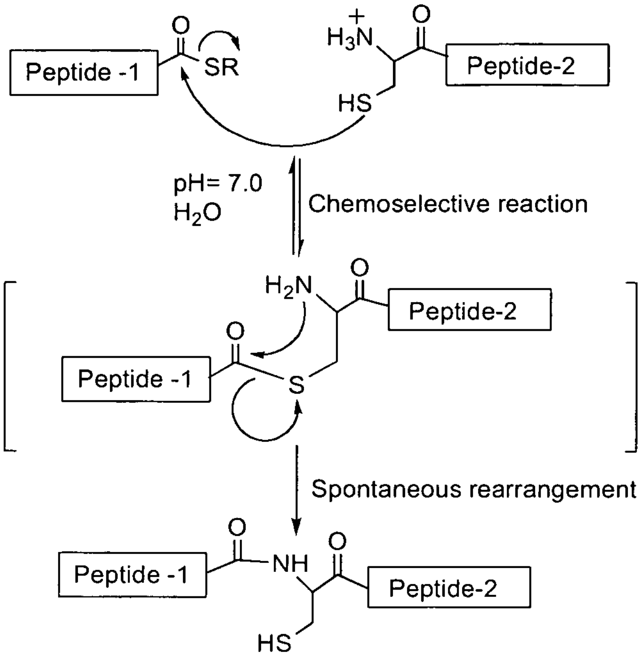
FIG. 1 shows an exemplary native chemical ligation between a C-terminal peptide thioester (peptide-1) and a peptide having an N-terminal cysteine (peptide-2).

Native chemical ligation (NCL), exemplified in FIG. 1, has proven inefficient or ineffective in the ligation of reactants that are poorly soluble in aqueous buffer. Such reactants include hydrophobic, nonpolar, or amphipathic compounds that tend not to dissolve well in water or have a low affinity for water. In the present invention, hydrophobic reactants are incorporated within liposomes, micelles, or other lipophilic structures, thereby allowing NCL of the hydrophobic reactants to proceed.

The method of the invention provides a novel method for ligation of first and second hydrophobic, nonpolar or amphipathic reactants. Unless otherwise indicated, the term “hydrophobic reactant” as used herein is inclusive of nonpolar and amphipathic reactants. Preferred hydrophobic reactants include lipophilic peptides, lipopeptides, glycopeptides, glycolipopeptides, lipidated amino acids and glycosylated amino acids.

A preferred method of the invention makes use of native chemical ligation (NCL). In this embodiment of the method, one of the hydrophobic reactants includes a thiol, preferably a terminal cysteine residue, more preferably an N-terminal cysteine residue, and the other hydrophobic reactant includes a thioester, preferably a C-terminal thioester.

More generally, the liposome-mediated ligation method of the invention can utilize any chemoselective ligation method amenable for the chemical ligation of reactants of interest, preferably hydrophobic reactants, including unprotected peptides, carbohydrates (oligosaccharides and polysaccharides), glycosylated or lipidated amino acids, glycopeptides, lipopeptides, glycolipopeptides, and lipids. Chemoselective ligations that can be employed in various embodiments of the method of the invention include, but are not limited to, oxime forming ligations, thio-ester forming ligations, thio-ether forming ligations, hydrazone forming ligations, thiazolidine forming ligations, oxazolidine forming ligations, and the Staudinger ligation, as well as ligation methods commonly referred to as "click-reactions" or "click-chemistry." (See, e.g., International Patent Publication WO 00/12536, published Mar. 9, 2000; Tam, 1996. *J. Immunol. Methods,* 196, 17-32; Hermanson, 1996. In Bioconjugate techniques pp 1-785, Academic Press; Kohn and Breinbauer, 2004. *Angew. Chem. Int. Ed.* 43, 3106-3116; Brase et al., 2005. *Angew. Chem. Int. Ed.,* 44, 5188-5240; and Kolb et al., 2001. *Angew. Chem. Int. Ed.* 40, 2004-2021). An exemplary "click reaction" is Huisgen cyclo-addition, which involves a reaction between an azide group and an alkyne group resulting in the formation of a triazole moiety. See Huisgen, 1,3-Dipolar Cycloaddition Chemistry-Introduction, Survey, Mechanism; 1984. in 1,3-*Dipolar Cycloaddition Chemistry* (Vol. 1) (Padwa, ed.) pp. 1-176, Wiley.

Table 1 shows exemplary chemoselective ligations that can be employed in the liposome-mediated ligation method of the invention. Functional groups 1 and 2 represent functional groups that are present in first or second reactants (without regard to order). X represents a halogen, e.g., F, Cl, Br or I, or any other displaceable leaving group. R can be H or any organic group, such as a linker molecule, an amino acid, a peptide, a glycosylated or lipidated amino acid, a glycopeptide, a lipid, a lipopeptide, a glycolipopeptide, or a carbohydrate (e.g., oligosaccharide or polysaccharide). R' can be H or any organic group, preferably an alkyl or aryl group. It is to be understood that for the oxime, hydrazone, thiazolidine, and oxazolidine formation reactions in Table 1, Functional group 1 is preferably an aldehyde or ketone. R" can be any organic group, preferably an alkyl, phenyl, benzyl, aryl, 2-(ethoxycarbonyl)ethyl, propionic acid, propionic amide or arylacetic acid.

TABLE 1

| Chemoselective ligations | | | |
|---|---|---|---|
| Reaction | Functional group 1 | Functional group 2 | Product |
| Thioalkylation Thioether formation | R—SH | 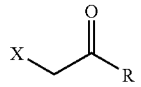 | 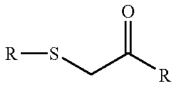 |
| Thiol addition Thioether formation | R—SH | 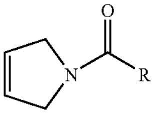 | 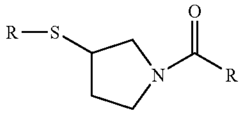 |
| Thioester formation | 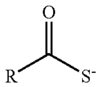 | 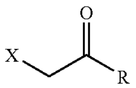 | 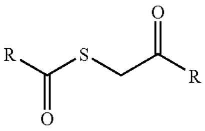 |
| Disulfide formation | R—SH | R'—SH | R—S—S—R' |
| Oxime formation | 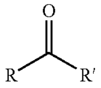 | 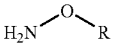 | 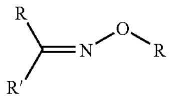 |
| Hydrazone formation | 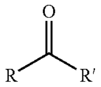 | 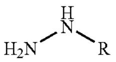 | 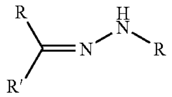 |
| Thiazolidine formation | 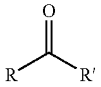 | 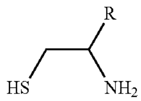 | 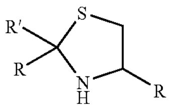 |
| Oxazolidine formation | 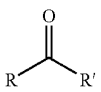 | 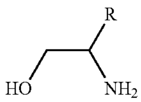 | 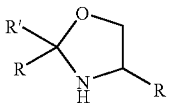 |

TABLE 1-continued

| Chemoselective ligations | | | |
|---|---|---|---|
| Reaction | Functional group 1 | Functional group 2 | Product |
| Huisgen cyclo-addition Triazole formation | R—$N_3$ | ≡—R | 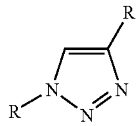 |
| Native Chemical Ligation (NCL) | 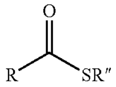 | 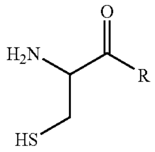 | 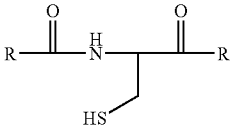 |

It should be understood that the reaction conditions and protocols set forth for the liposome-mediated NCL in the Examples and elsewhere herein can be used or modified for use in the ligation reactions listed in Table 1. One of skill in the art can readily modify or optimize the reaction conditions for a particular ligation reaction. Reaction conditions that can be so modified include, but are not limited to, pH, temperature, lipid components, ratio of lipids to ligation reactants, concentration of ligation reactants, and reaction medium (buffers, solvents or, water or buffer content in solvent mixtures).

Optionally, the solubility of the reactants and the lipid structure (i.e., liposomes (bilayers), micelles (monolayers) or other lipid structures such as films, emulsions, gels and matrices) is manipulated or enhanced by the addition or exclusion of reagents that assist in solubilizing the lipid matrix and the ligation reactants. Solubilizing reagents can be used to manipulate, control, and/or optimize the formation of the lipid structure and/or insertion of the reactants into the lipid structure. The optimization of reaction conditions can be determined using standard chemical and biochemical analysis methods including, but not limited to, reverse phase high performance liquid chromatography (RP-HPLC), high pH anion exchange chromatography with pulsed amperometric detection (HPAEC-PAD), nuclear magnetic resonance (NMR), and mass spectrometry (MS).

The method of the invention involves contacting first and second reactants with a lipid or lipidic structure, e.g., a membrane, under conditions to allow chemoselective ligation, preferably native chemical ligation, of the first reactant and the second reactant to yield a multicomponent compound comprising the first and second reactant.

In one embodiment, the reactants are contacted with the components of the lipid structure prior to formation of the lipid structure. The resulting mixture is then subjected to physical or chemical conditions so as to allow the formation of a lipidic structure, such as a bilayer, monolayer, micelle, liposome, film, emulsion, matrix or gel. Methods for making lipid bilayers, monolayers, liposomes, micelles, films, matrices, gels and emulsions are well known to the art, and the invention is not intended to be limited by the method for making the lipidic structure.

In another embodiment, the reactants are contacted with a preformed lipid structure, then the mixture is subjected to physical or chemical conditions so as to allow for the solubilization of the reactants in the lipidic phase. For example, the mixture can be shaken, sonicated, heated or the like to fully solubilize the reactants. Optionally, the preformed lipid structure can contain at least one of the reactants, and other reactant(s) can be contacted with the preformed lipid structure and solubilized in the lipid phase.

Optionally, the ligation reaction is initiated with an initiator or catalyst. Preferred initiators are sulfur-containing compounds such as thiols, including thiophenol, substituted thiophenols such as 4-carboxylmethylthiophenol, thiophenol/benzyl mercaptan, 2-mercaptoethanesulfonate, or sodium-2-mercaptoethane sulfonate. However, it has been found (see Example III) that the ligation reaction proceeds within the lipidic structure even without the addition of a catalyst. Thus, the ligation method of the invention can be practiced with or without a catalyst.

If a catalyst is used, the ligation reaction is preferably not initiated until both reactants are solubilized in the lipid phase; i.e., neither reactant remains in the aqueous phase. The ligation reaction preferably takes place within the lipid phase, as discussed in more detail below.

The present invention utilizes lipid solubilization is used to facilitate chemoselective ligation, preferably native chemical ligation, involving hydrophobic, nonpolar, or amphipathic reactants. Lipids are examples of hydrophobic compounds. Glycolipids, glycopeptides, and phospholipids are examples of amphipathic compounds. Amphipathic compounds contain both hydrophobic and hydrophilic parts. The word amphipathic is used interchangeably with the word amphiphilic. Further, as noted above, unless otherwise indicated the term “hydrophobic reactant” as used herein is inclusive of nonpolar and amphipathic reactants. Most hydrophobic, nonpolar and amphipathic reactants are lipophilic, tending to dissolve in, having a strong affinity for, or readily mixing with lipids or other substances of low polarity. Lipophilic reactants are preferred for use in the method of the invention.

In the present invention, chemoselective ligation, such as native chemical ligation, takes place in a lipid phase, preferably within a lipidic structure. The molecular components of a lipid phase may be ordered or disordered. The lipidic structure can be a planar or sheet-type structure; it can take the form of a closed structure, such as a sphere; it can constitute a lipid or lipophilic emulsion, film, matrix or gel; or it can take a more complex form, such as a cubic lipidic phase (Hunter et al., Bioconjugate Chem., 2004, 15:3; U.S. Pat. Publ. 20030018169, published Jan. 23, 2003). The lipidic structure can take the form of a monolayer (e.g., a spherical monolayer structure such as a micelle), a bilayer (e.g., a spherical bilayer structure such as a liposome) or it can include additional layers. The lipidic structure is also referred to herein as a membrane or lipidic membrane.

The lipidic structure may be formed from one or more types of naturally occurring or synthetic nonpolar, hydrophobic or amphipathic molecules, such as amphipathic detergents, phospholipids, glycolipids, sterols such as cholesterols, synthetic amphipathic polymers and the like. It should be understood that the invention is not limited by the composition of the lipidic structure. Suitable phospholipids include, without limitation, naturally occurring or synthetic phospholipids, including derivatized forms thereof. Common phospholipids suitable for use in forming the lipidic structure include phosphatidylcholine (lecithin) (PC), phosphatidylglycerol (PG), phosphatidic acid (PA), diphosphatidylglycerol (cardiolipin), phosphatidyl-inositol (PI), phosphatidylethanolamine (PE), phosphatidylserine (PS), sphingolipids such as sphingomyelin, and their analogs and derivatives as well as their lysophospholipid counterparts in which one of the acyl substituents is missing. Phospholipid derivatives can have, for example, one or more saturated acyl groups, unsaturated acyl groups, or mixed acyl groups. Furthermore, derivatizations at the acyl groups of the phospholipid can be symmetric or asymmetric (such as POPC, 1-palmitoyl-2-oleoyl phosphatidylcholine). Additional exemplary components of the lipidic structure include, without limitation, dodecylphosphocholine and phosphocholine. Optionally phospholipids and other membrane components can be derivatized with polyethylene glycol (PEGylated) or other polymers.

Examples of phosphatidylcholines for use in preparation of the lipidic structure include DOPC, dioleoylphosphatidylcholine; DEPC, dierucoylphosphatidylcholine; DDPC, didecanoylphosphatidylcholine; DLPC, dilauroylphosphatidylcholine; DMPC, dimyristoylphosphatidylcholine; DPPC, dipalmitoylphosphatidylcholine; DSPC, distearoylphosphatidylcholine; and DLoPC, dilinoleoyl phosphatidylcholine. Examples of phosphatidylglycerols for said use include DLPG, dilauroyl phosphatidylglycerol; DMPG, dimyristoyl phosphatidylglycerol; DPPG, dipalmitoyl phosphatidylglycerol; DSPG, distearoyl phosphatidylglycerol; DOPG, dioleoyl phosphatidylglycerol; and DEPG, dierucoyl phosphatidylglycerol. Examples of phosphatidic acids include DLPA, dilauroyl phosphatidic acid; DMPA, dimyristoyl phosphatidic acid; DPPA, dipalmitoyl phosphatidic acid; and DSPA, distearoyl phosphatidic acid. Examples of phosphatidylethanolamines include DLPE, dilauroyl phosphatidylethanolamine; DMPE, dimyristoyl phosphatidylethanolamine; DPPE, dipalmitoyl phosphatidylethanolamine; DSPE, distearoyl phosphatidylethanolamine; DOPE, dioleoyl phosphatidylethanolamine; and DEPE, dierucoyl phosphatidylethanolamine. Examples of phosphatidylserines include DLPS, dilauroyl phosphatidylserine; DPPS, dipalmitoyl phosphatidylserine; DMPS, dimyristoyl phosphatidylserine; DSPS, distearoyl phosphatidylserine; and DOPS, dioleoyl phosphatidylserine. An example of a sphingomyelin derivative is dihidrosphingomyelin.

In a preferred embodiment, NCL is performed in the presence of a micelle (a vesicle formed from a lipid monolayer) or a liposome (a vesicle formed from a lipid bilayer). It should be understood that the term "liposome-mediated" ligation, as used herein, is intended to include ligations that are mediated by liposomes (bilayers), micelles (monolayers) or other lipid structures such as films, emulsions, gels and matrices.

Advantageously, the liposome, micelle or other lipidic structure within which the ligation is performed can be used as a delivery vehicle for administration of a therapeutic ligation product to a patient in need thereof.

It was observed that reaction rates of liposome-mediated NCL are substantially higher than traditional reaction conditions, resulting in improved yields. Without intending to be bound by theory, NCL in the presence of a lipid structure such as a liposome or micelle is believed to reduce nonspecific aggregation of the hydrophobic reactants and provide better access to the hydrophobic reactant for ligation. The ligation reactions described in Example 1 take place in the lipid environment, and the relative high reaction rate of the liposome-mediated NCL is likely due to a relatively high local concentration of reactants.

In a particularly preferred embodiment of the method of the invention, the ligation of the reactants takes place within the lipidic phase, e.g., the lipid bilayer or monolayer, as opposed to at the interface between the membrane structure and the external, aqueous solution. More specifically, the functional groups involved in the ligation reaction, e.g., the thioester and the cysteine, are solubilized within the lipid phase. When the reaction takes place within the lipidic phase, both the thioester of the first reactant and the sulfhydryl group from the N-terminal cysteine residue of the second reactant are embedded within the membrane structure, in contrast to surface ligation as shown, for example, in Otaka et al. (Chem Commun., 2004, 1722-1723).

Figure 2:
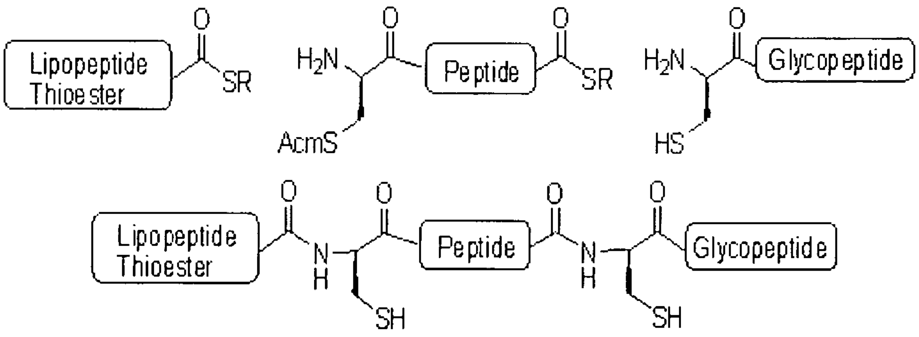
FIG. 2 shows a general schematic of (a) exemplary reactants; and (b) a three-component vaccine synthesized from those reactants using liposome-mediated chemical ligation.

The method of the invention is useful for chemoselective ligation, particularly native chemical ligation, using one or more hydrophobic or lipophilic reactants, without limitation. The method is particularly useful in methods involving the ligation of one or more biomolecules, such as hydrophobic peptides, lipids, phospholipids, steroids, triglycerides, glycopeptides, lipopeptides, and glycolipopeptides. In a particularly preferred embodiment, the method is used to synthesize lipidated carbohydrates, such as lipidated glycopeptides as exemplified in Example I. Lipidated carbohydrates, including lipidated glycopeptides, that are synthesized according to the method of the invention (see FIG. 2 for a general synthetic scheme) can be useful as vaccines, as further described in international patent application PCT/US2007/000158, filed Jan. 3, 2007, and Buskas et al., Angew. Chem., Int. Ed. 2005, 44, 5985-5988.

In a preferred method involving native chemical ligation, one or more of the reactants is optionally derivatized prior to ligation so as to add a C-terminal thioester and/or an N-terminal cysteine residue, as needed, in order to facilitate the native chemical ligation reaction.

In a preferred embodiment, the method of the invention is used to synthesize a compound that contains one or more carbohydrate components, one or more peptide components, and/or one or more lipid components. The individual components or "building blocks" to be assembled into a multi-component compound using the method of the invention can be chemically, enzymatically or biologically synthesized, without limitation, and may include one or more protecting groups that can be removed during a later step in a multi-step synthesis. A carbohydrate component that is chemically synthesized can, for example, contain an acetyl ester that is subsequently removed prior to or during the process of liposome-mediated native chemical ligation. The method of the invention can be used in a single step to synthesize a compound containing two or more components, or it can be used in multiple steps to synthesize a compound containing three or more components.

Examples of suitable carbohydrate components include oligosaccharides, polysaccharides and monosaccharides, and glycosylated biomolecules (glycoconjugates) such as glycoproteins, glycopeptides, glycolipids, glycosylated amino acids, DNA, or RNA. Glycosylated peptides (glycopeptides)

and glycosylated amino acids, which contain one or more carbohydrate moieties as well as a peptide or amino acid, are particularly preferred as the carbohydrate component of the ligation product. An example of a glycopeptide is CD52, which is expressed on virtually all human lymphocytes and believed to play an important role in the human immune system. An example of a glycosylated amino acid is the Tn antigen. It should be understood that when the carbohydrate component is a glycopeptide, the peptide part of the glycopeptide optionally includes a T-epitope and thus may serve as a peptide component of the glycolipopeptide.

The carbohydrate component of the ligation product, if present, includes a carbohydrate that contains one or more saccharide monomers. For example, the carbohydrate can include a monosaccharide, a disaccharide or a trisaccharide; it can include an oligosaccharide or a polysaccharide. An oligosaccharide is an oligomeric saccharide that contains two or more saccharides and is characterized by a well-defined structure. A well-defined structure is characterized by the particular identity, order, linkage positions (including branch points), and linkage stereochemistry (α, β) of the monomers, and as a result has a defined molecular weight and composition. An oligosaccharide typically contains about 2 to about 20 or more saccharide monomers. A polysaccharide, on the other hand, is a polymeric saccharide that does not have a well defined structure; the identity, order, linkage positions (including brand points) and/or linkage stereochemistry can vary from molecule to molecule. Polysaccharides typically contain a larger number of monomeric components than oligosaccharides and thus have higher molecular weights. The term "glycan" as used herein is inclusive of both oligosaccharides and polysaccharides, and includes both branched and unbranched polymers. When the carbohydrate component contains a carbohydrate that has three or more saccharide monomers, the carbohydrate can be a linear chain or it can be a branched chain. In a preferred embodiment, the carbohydrate component contains less than about 15 saccharide monomers; more preferably in contains less than about 10 saccharide monomers.

The carbohydrate component of the glycolipopeptide includes a carbohydrate that contains a B-epitope. The B-epitope can be a naturally occurring epitope or a non-naturally occurring epitope. Preferably, two or more saccharide monomers of the carbohydrate interact to form a conformational epitope that serves as the B-epitope. A B-epitope is an epitope recognized by a B cell. Any antigenic carbohydrate that contains a B-epitope can be used as the carbohydrate component, without limitation.

In one embodiment, the carbohydrate component contains all or part of a self-antigen. Self-antigens are antigens that are normally present in an animal's body. They can be regarded as "self-molecules," e.g., the molecules present in or on the animal's cells, or proteins like insulin that circulate in the animal's blood. An example of a self-antigen is a carbohydrate-containing component derived from a cancer cell of the animal, such as a tumor-associated carbohydrate antigen (TACA). Typically, such self-antigens exhibit low immunogenicity. Examples include tumor-related carbohydrate B-epitope such as $Le^y$ antigen (a cancer related tetrasaccharide; e.g., Fucα((1,2)-Galβ(1,4)-[Fucα(1,3)]-GalNAc); Globo-H antigen (e.g., Fucα(1,2)-Galβ(1,3)-GalNAcβ(1,3)-Galα(1,4)-Galβ(1,4)-Glu); T antigen (e.g., Galβ(1,3)-GalNAcα-O-Ser/Thr); STn antigen (sialyl Tn, e.g., NeuAcα(2,6)-GalNAcα-O-Ser/Thr); and Tn antigen (e.g., α-GalNAc-O-Ser/Thr). Another example of a self-antigen is a glycopeptide derived from the tandem repeat of the breast tumor-associated MUC-1 of human polymorphic epithelial mucin (PEM), an epithelial mucin (Baldus et al., Crit. Rev. Clin. Lab. Sci., 41(2): 189-231 (2004)). A MUC-1 glycopeptide comprises at least one Tn and/or sialyl Tn (sialyl α-6 GalNAc, or "STn") epitope; preferably linked to a threonine (T-Tn or T-STn).

Structures of exemplary tumor-associated carbohydrate antigens (TACA) that can be used as a component of the glycolipopeptide include, without limitation, the structures shown below.

Tn, STn, and TF antigens

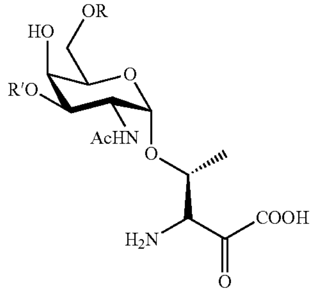

1. R = H, R' = H

2. R= 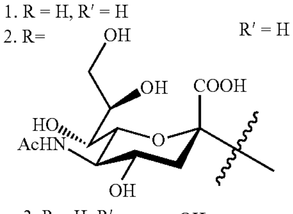 R' = H

3. R = H, R' = 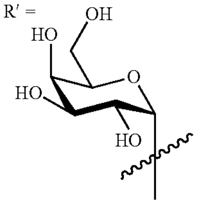

-continued

Tn3, STn3, and TF3

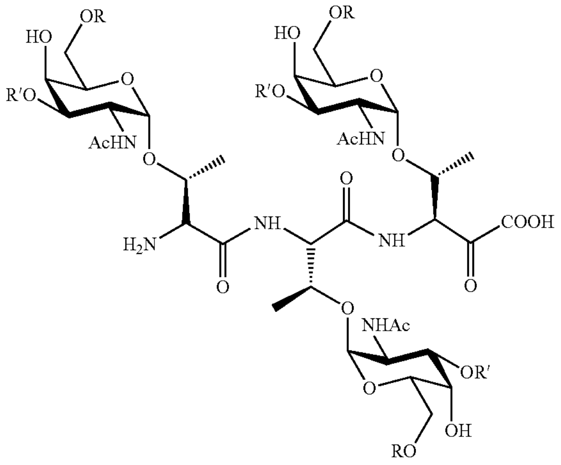

4. R = H, R' = H

5. R= R' = H

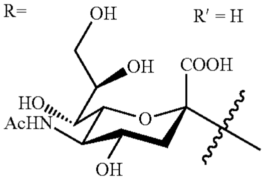

6. R = H, R' =

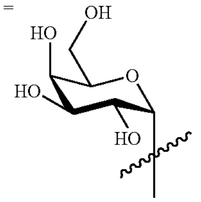

-continued

MUC-1 with Tn, STn, and TF

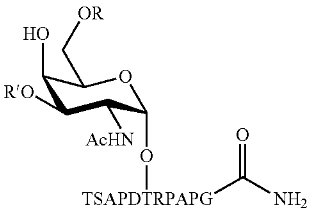

7. R = H, R' = H

8. R= R' = H

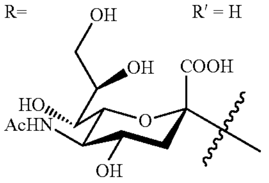

9. R = H, R' =

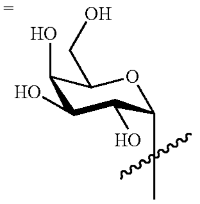

It should be noted that the Tn, STn, and TF structures shown in above (monomeric, trimeric, clustered) are all shown with a threonine residue. The corresponding serine analogues are also suitable structures. In the case of Tn3, STn3, TF3 and their respective clusters, all possible homo- and hetero-analogues with differences in the threonine/serine composition of the backbone are included.

Lewis' and SLewis'

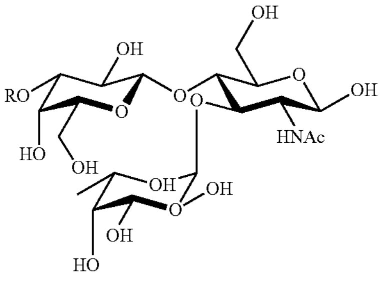

14. R = H

15. R=

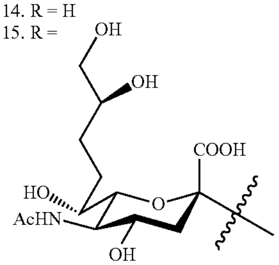

Lewis$^y$ and SLewis$^y$

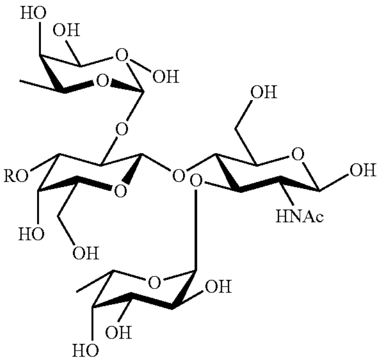

10. R =11

11. R=

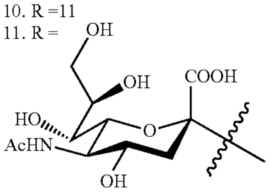

-continued

Lewis$^y$–lactose and SLewis$^y$–lactose

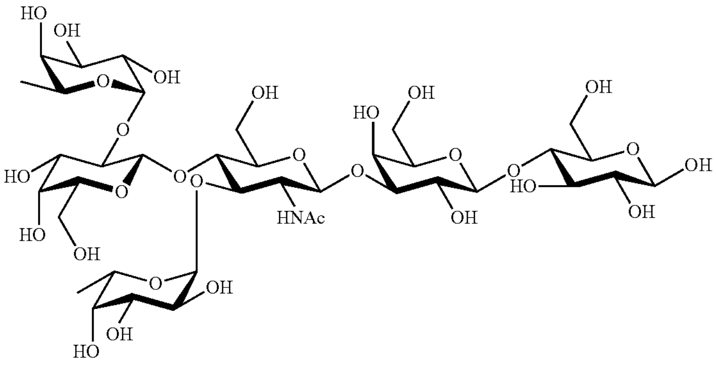

12. R =11

13. R =

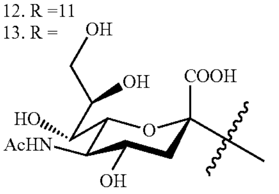

Lewis$^y$–Lewis$'$ dimer

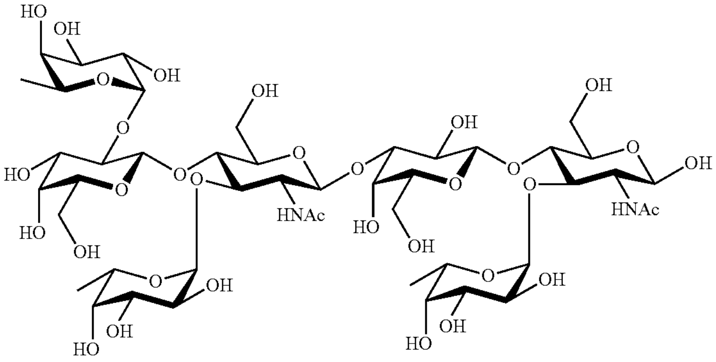

The KH-1 antigen

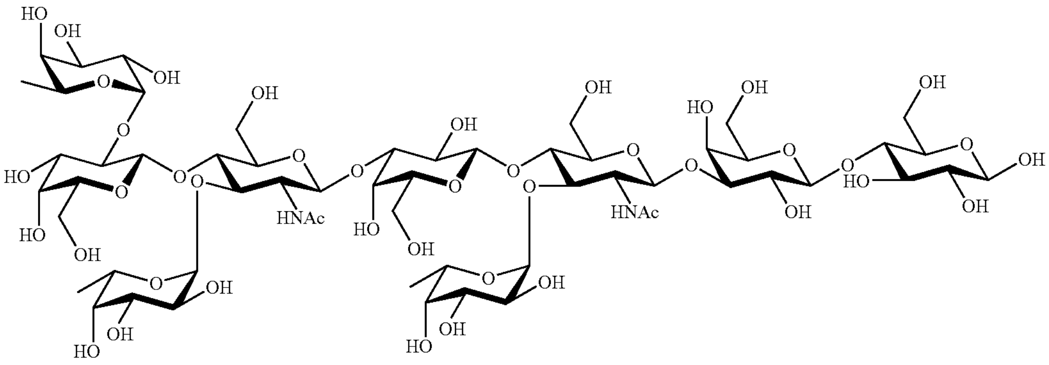

In another embodiment, the carbohydrate component contains all or part of a carbohydrate antigen (typically a glycan) from a microorganism, preferably a pathogenic microorganism, such as a virus (e.g., a carbohydrate present on gp120, a glycoprotein derived from the HIV virus), a Gram-negative or Gram-positive bacterium (e.g., a carbohydrate derived from *Haemophilus influenzae, Streptococcus pneumoniae*, or *Neisseria meningitides*), a fungus (e.g., a 1,3-β-linked glucan) a parasitic protozoan (e.g., a GPI-anchor found in protozoan parasites such as *Leishmania* and *Trypanosoma brucei*), or a helminth. Preferably, the microorganism is a pathogenic microorganism.

An exemplary glycan from viral pathogens, Man9 from HIV-1 gp120, is shown below.

Man9 from HIV-1 gp 120

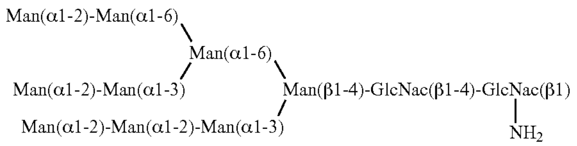

Exemplary HIV carbohydrate and glycopeptide antigens are described in Wang et al. (Current Opinion in Drug Disc. & Develop., 9(2): 194-206 (2006)) and Warren et al. (Top. Curr Chem 2007, 267: 109-141), and include both naturally occurring HIV carbohydrates and glycopeptides, as well as synthetic carbohydrates and glycopeptides based on naturally occurring HIV carbohydrates and glycopeptides.

Exemplary HCV carbohydrate and glycopeptide antigens are described in Koppel et al. *Cellular Microbiology* 2005; 7(2): 157-165 and Goffard et al. *J. of Virology* 2005; 79(13): 8400-8409, and include both naturally occurring HCV carbohydrates and glycopeptides, as well as synthetic carbohydrates and glycopeptides based on naturally occurring HCV carbohydrates and glycopeptides.

Exemplary glycans from bacterial pathogens are shown in below.

*Haemophilus influenzae* Type b, CPS repeating unit

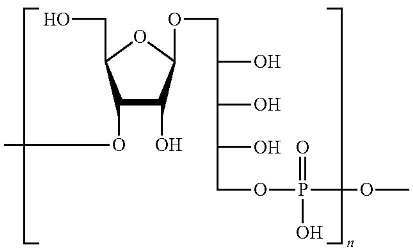

Group B type III *Streptococcus*

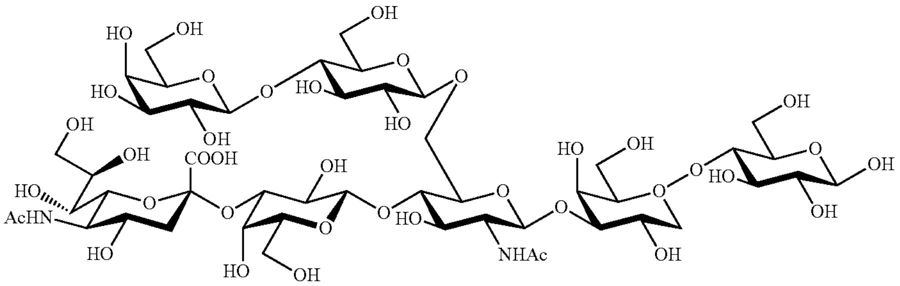

Cell-wall Carbohydrates from *Bacillus anthracis, Ames, Sterne, Pasteur*

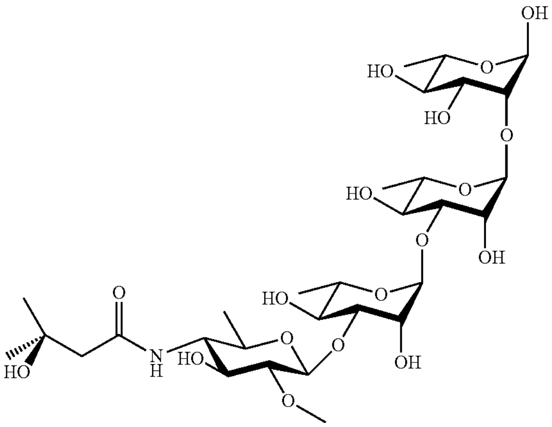

-continued
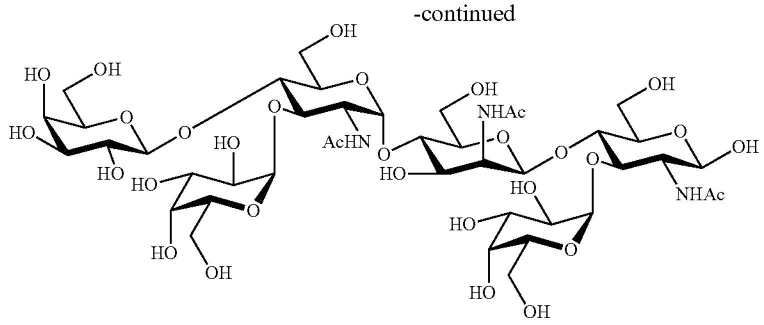
*Francisella tularencis*, Core region and O-side chain repeating unit
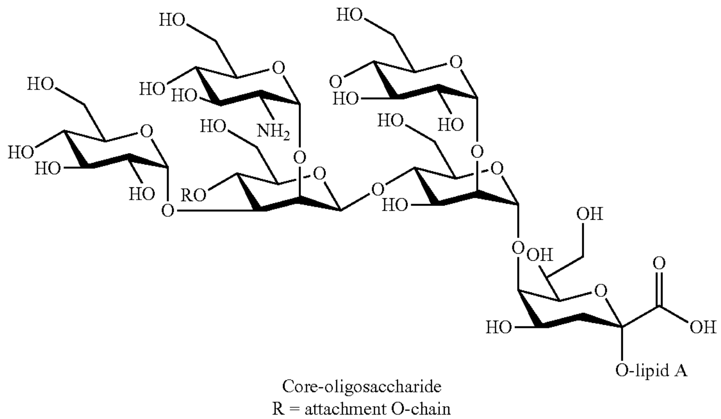
Core-oligosaccharide
R = attachment O-chain
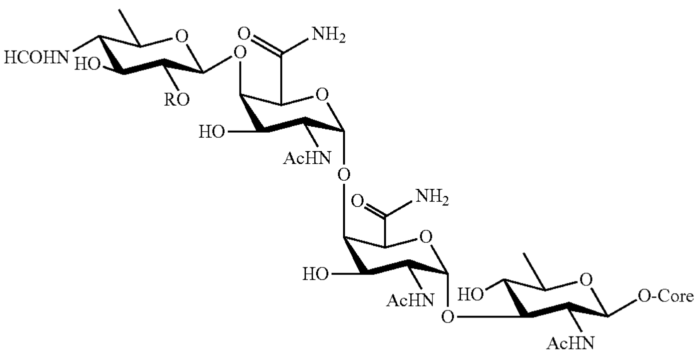
Repeating unit of O-chain
(R = extension point)
*Burkholdaria pseudomallei*. exo-polysaccharide
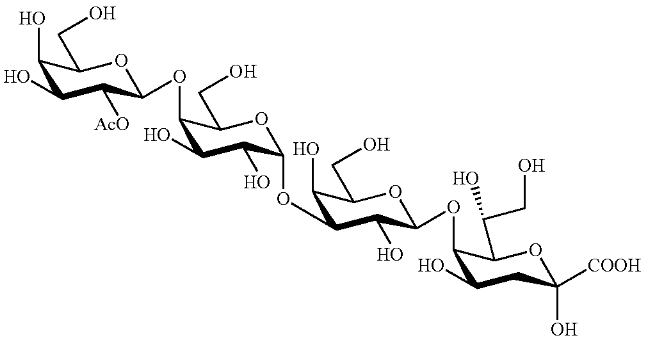
Exemplary glycans from protozoan pathogens are shown below.

*Plasmodium falsiparum*, Malaria parasite

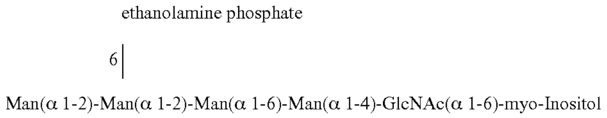

*Leishmania* species antigenic glycan

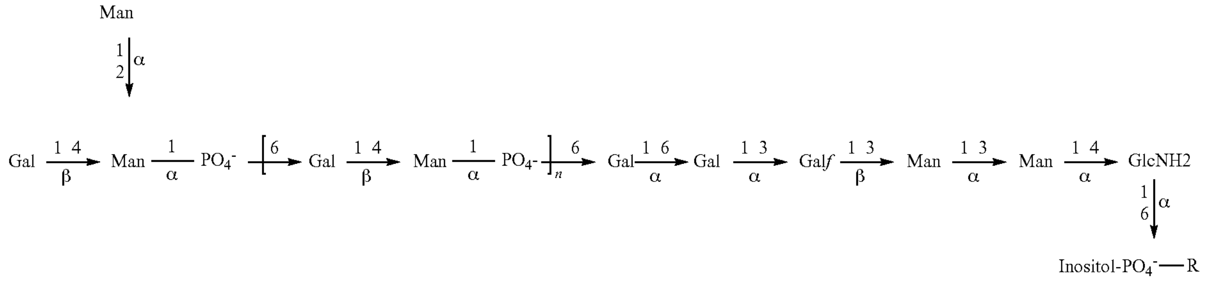

*Trypanozoma cruzi*

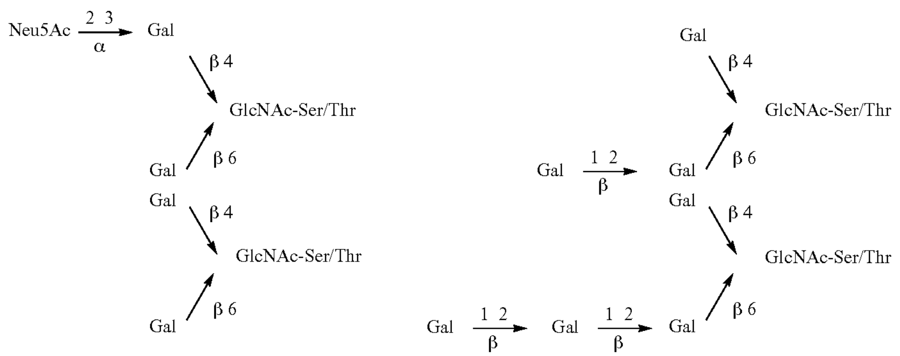

An exemplary glycan from a fungal pathogen is shown below.

*Cryptococcus neoformans* Capsular polysaccharide

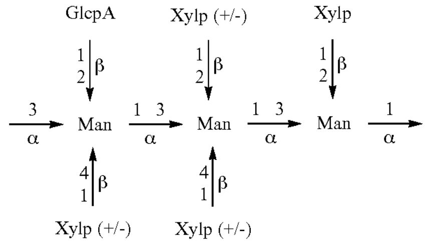

An exemplary glycan from helminth pathogen is shown below.

*Schistosoma*

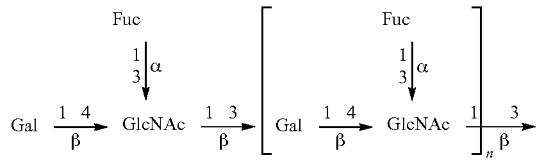

It will be appreciated by one of skill in the art that while numerous antigenic carbohydrate structures are known, many more exist, since only a small fraction of the antigenic or immunogenic carbohydrates have been identified thus far. Examples of the many carbohydrate antigens discovered thus far can be found in Kuberan et al., Curr. Org. Chem, 4, 653-677 (2000); Ouerfelli et al., Expert Rev. Vaccines 4(5): 677-685 (2005); Hakomori et al., Chem. Biol. 4, 97-104 (1997); Hakomori, Acta Anat. 161, 79-90 (1998); Croce and Segal-Eiras,. "The use of carbohydrate antigens for the preparation of vaccines for therapy in breast cancer," Drugs of Today 38(11):759-768 (2002); Mendonca-Previato et al., Curr Opin. Struct. Biol. 15(5):499-505 (2005); Jones, Anais da Academia Brasileira de Ciencias 77(2):293-324 (2005); Goldblatt, J. Med. Microbiol. 47(7):563-567 (1998); Diekman et al., Immunol. Rev., 171: 203-211, 1999; Nyame et al., Arch. Biochem. Biophys., 426 (2): 182-200, 2004; Pier, Expert Rev. Vaccines, 4 (5): 645-656, 2005; Vliegenthart, FEBS Lett., 580(12): 2945-2950, Sp. Iss., 2006; Ada et al., Clin. Microbiol. Inf., 9 (2): 79-85, 2003; Fox et al., J. Microbiol. Meth., 54 (2): 143-152, 2003; Barber et al., J. Reprod. Immunol., 46 (2): 103-124, 2000; and Sorensen, Persp. Drug Disc. Design, 5: 154-160, 1996. Any antigenic carbohydrate derived from a mammal or from an infectious organism can be used as a carbohydrate component, without limitation.

The peptide component, if present in the ligation product, can be any peptide-containing structure, and can contain naturally occurring and/or non-naturally occurring amino acids and/or amino acid analogs (e.g., D-amino acids). The peptide component advantageously may include a T-epitope, preferably a helper T epitope. Preferably the peptide component contains less than about 20 amino acids and/or amino acid analogs. Examples of peptide components include the universal helper T peptide, QYIKANSKFIGITEL ("QYI") (SEQ ID NO:1), the universal helper T peptide YAFKYARHANVGRNAFELFL ("YAF") (SEQ ID NO:2), the murine helper T peptide KLFAVWKITYKDT ("KLF") (SEQ ID NO:3) derived from polio virus, and pan-DR binding (PADRE) peptides (PCT WO 95/07707; Alexander et al., Immunity 1:751-761 (1994); Alexander et al., J. Immunol. 2000 Feb. 1; 164(3):1625-33; U.S. Pat. No. 6,413,935 (Sette et al., Jul. 2, 2002)).

Preferred immunogenic peptide components for use in a glycolipopeptide ligation product include universal (degenerate or "promiscuous") helper T-cell peptides, which are peptides that are immunogenic in individuals of many major histocompatibility complex (MHC) haplotypes. Numerous universal helper T-cell peptide structures are known; however, it should be understood that additional universal T-epitopes, including some with similar or even higher potency, will be identified in the future, and such peptides are well-suited for use as the peptide component.

Exemplary T-cell peptides for use in the glycolipopeptide include, without limitation:

Synthetic, nonnatural PADRE peptide, DAla-Lys-Cha-Val-Ala-Ala-Trp-Thr-Leu-Lys-Ala-Ala-DAla, including all the analogues described by Alexander et al. in Immunity, 1:751-761, 1994.

Peptides derived from tetanus toxin, e.g., (TT830-843) QYIKANSKFIGITEL (SEQ ID NO:1), (TT1084-1099) VSIDKFRIFCKANPK (SEQ ID NO:4), (TT11174-1189) LKFIIKRYTPNNEIDS (SEQ ID NO:5), (TT1064-1079) IREDNNITLKLDRCNN (SEQ ID NO:6), and (TT947-967) FNNFTVSFWLRVPKVSASHLE (SEQ ID NO:7);

Peptides derived from polio virus, e.g., KLFAVWKITYKDT (SEQ ID NO:3);

Peptides derived from *Neisseria meningitidis*, e.g.,

```
YAFKYARHANVGRNAFELFL;       (SEQ ID NO: 2)
and
```

Peptides derived from *P. falsiparum* CSP, e.g.,

```
EKKIAKMEKASSVFNVNN          (SEQ ID NO: 8)
```

The peptide component of a glycolipopeptide ligation product may contain a T-epitope. A T-epitope is an epitope recognized by a T cell. The T-epitope can elicit a CD4+ response, thereby stimulating the production of helper T cells; and/or it can elicit a CD8+ response, thereby stimulating the production of cytotoxic lymphocytes. Preferably, the T-epitope is an epitope that stimulates the production of helper T cells (i.e., a helper T-cell epitope or Th-epitope), which in turn make possible a humoral response to the B-epitope supplied by the carbohydrate component.

It should be understood that a glycolipopeptide ligation product can contain multiple T-epitopes, which may be the same or different. Further, T-epitopes may be present on the carbohydrate component and/or the lipid component (e.g., in embodiments that include glycopeptides and/or glycolipids as the carbohydrate and/or lipid components) in addition to, or in place of, the peptide component.

In one embodiment, the B-epitopes and the T-epitopes are homologous; that is, they are derived from the same organism. For example, in a glycolipopeptide suitable for use as a vaccine against a microbial pathogen, the T-epitope in addition to the B-epitope may be epitopes that are present in the microbial pathogen. In another embodiment, the B-epitopes and the T-epitopes are heterologous; that is, they are not derived from the same organism. For example, a glycolipopeptide suitable for use as an anti-cancer vaccine may have a B-cell epitope from a cancer cell, but a T-cell epitope from a bacterium or virus.

The lipid component, if present in the ligation product, can be any lipid-containing component, such as a lipopeptide, fatty acid, phospholipid, steroid, or a lipidated amino acids and glycolipids such as Lipid A derivatives. In some embodiments, the lipid component is non-antigenic; that is, it does not elicit antibodies directed against specific regions of the lipid component. However, the lipid component may and preferably does serve as an immunoadjuvant. The lipid component can serve as a carrier or delivery system for the multi-epitopic glycolipopeptide. It assists with incorporation of the glycolipopeptide into a vesicle such as a liposome or micelle to facilitate delivery of the glycolipopeptide to a target cell, and it enhances uptake by target cells, such as dendritic cells. Further, the lipid component stimulates the production of cytokines.

One class of preferred lipid components for use in the ligation product comprises molecular ligands of the various Toll-like receptors (TLRs). There are many known subclasses of Toll-like receptors (e.g., TLR1, TLR2, TRL3, TLR4, TLR5, TLR6, TLR7, TLR8, TLR9, TLR10, TLR11, TLR12, TLR13, TLR14, TLR15 and TLR16). See Roach et al., PNAS 2005, 102:9577-9582, for a review of the relationships between and evolution of Toll-like receptors; and Duin et al., TRENDS Immunol., 2006, 27:49-55, for a discussion of TLR signaling in vaccination. Particularly preferred are lipid components that interact with TLR2 and TLR4. TLR2 is involved in the recognition of a wide array of microbial molecules from Gram-positive and Gram-negative bacteria, as well as mycoplasma and yeast. TLR2 ligands include lipoglycans, lipopolysaccharides, lipoteichoic acids and peptidoglycans. TLR4 recognizes Gram-negative lipopolysaccharide (LPS) and lipid A, its toxic moiety. TLR ligands are widely available commercially, for example from Apotech and InvivoGen. Preferably, the lipid component is a TLR ligand that facilitates uptake of the glycolipopeptide by antigen presenting cells.

Suitable lipids for use as the lipid component of a ligation product include PamCys-type lipid structures, such as those derived from $Pam_3Cys$ (S—[(R)-2,3-dipalmitoyloxy-propyl]-N-palmitoyl-(R)-cysteine) and $Pam_2Cys$ (S—[(R)-2,3-dipalmitoyloxy-propyl]-(R)-cysteine), which lacks the N-palmitoyl group of $Pam_3Cys$. $Pam_3Cys$ and $Pam_2Cys$ are derived from the immunologically active N-terminal sequence of the principal lipoprotein of *Escherichia coli*. This class of lipids also includes $Pam_3CysSK_4$ (N-palmitoyl-S—[(R)-2,3-bis(palmitoyloxy)-propyl]-(R)-cysteinyl-(S)-seryl-(S)-lysine-(S)-lysine-(S)-lysine-(S)-lysyne) and $Pam_2CysSK_4$ (S—[(R)-2,3-bis(palmitoyloxy)-propyl]-(R)-cysteinyl-(S)-seryl-(S)-lysine-(S)-lysine-(S)-lysine-(S)-lysyne), which lacks the N-palmitoyl group of $Pam_3CysSK_4$; it should be understood that the number of lysines in these structures can be 0, 1, 2, 3, 4, 5 or more (i.e., $K_n$ where n=0, 1, 2, 3, 4, 5 or more).

Another preferred class of lipids includes Lipid A (LpA) type lipids, such as Lipid As derived from *E. coli, S. typhimurium* and *Neisseria meningitidis*. The Lipid As can be attached to the carbohydrate component (containing a B-epitope) of the glycolipopeptide and/or to the peptide component (containing a T-epitope) through a linker that is connected, for example, to the anomeric center or anomeric phosphate, the C-4' phosphate or the C-6' position. The phosphates can be modified, for example, to include one or more phosphate ethanolamine diesters. Exemplary Lipid A derivatives are described in, for example, Caroff et al., Microbes Infect. 4, 915-926 (2002); Raetz et al., Annu. Rev. Biochem. 71, 635-700 (2002); and Dixon et al., J. Dent. Res. 84, 584-595 (2005).

Advantageously, the method of the invention allows multiple-component compounds to be synthesized using a modular approach. For example, first and second components can be ligated using liposome-mediated chemoselective ligation, preferably native chemical ligation, to yield a two-component ligation product. The two-component ligation product is then used as a reactant in a second round of liposome-mediated chemoselective ligation, preferably native chemical ligation with a third component to yield a three-component ligation product. This allows a modular approach to be used to screen for, or synthesize, various vaccines or vaccine candidates. An array of B- and T-epitopes and lipopeptides can be made available, including two-component modules that include, for example, selected B- and T-epitopes, or a selected T-epitope and a selected lipopeptide adjuvant. Then, custom compounds can be built by combining the desired modules. The method the invention, liposome-mediated chemoselective ligation, preferably native chemical ligation, can be used to synthesize two-component modules and/or the final compound. Alternatively or additionally, liposome-mediated chemoselective ligation, preferably native chemical ligation, can be precede or succeed other ligation methods in a multiple step synthesis to produce the final multi-component compound. A modular approach is attractive because it provides greater synthetic flexibility than linear synthesis. Each building block can be used for the preparation of several different target compounds.

EXAMPLES

The present invention is illustrated by the following examples. It is to be understood that the particular examples, materials, amounts, and procedures are to be interpreted broadly in accordance with the scope and spirit of the invention as set forth herein.

Example I

Figure 3:
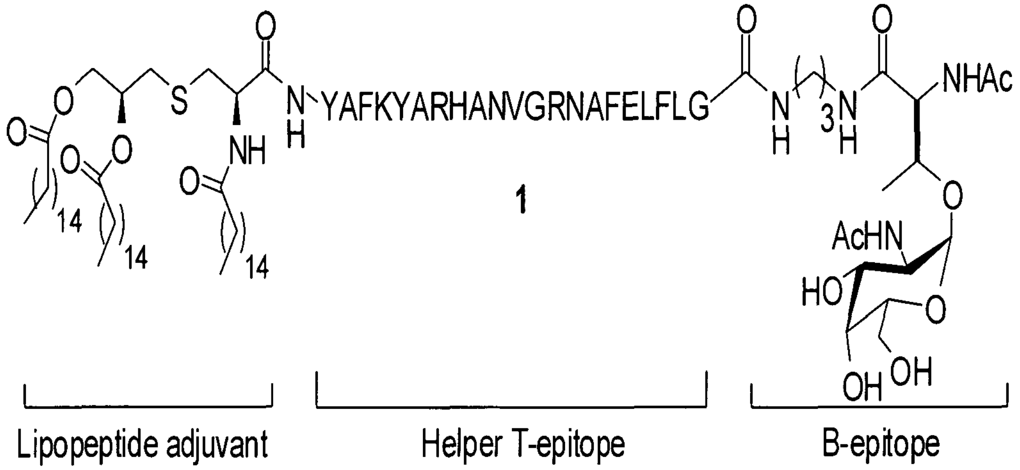
FIG. 3 shows an exemplary three-component glycolipopeptide vaccine 1.

Synthesis of a Three-Component Vaccine Using Liposome-Mediated Native Chemical Ligation Recently, we demonstrated (Buskas et al., Angew. Chem., Int. Ed. 2005, 44, 5985-5988) that the three-component vaccine candidate 1 (FIG. 3) composed of the tumor-associated Tn-antigen (Springer, Science 1984, 224, 1198-1206; Kagan et al., Cancer Immunol. Immunother. 2005, 54, 424-430; Toyokuni et al., J. Am. Chem. Soc. 1994, 116, 395-396), the peptide T-epitope YAFKYARHANVGRNAFELFL (SEQ ID NO:2; YAF) (Wiertz et al., J. Exp. Med. 1992, 176, 79-88), and the lipopeptide S-[(R)-2,3-dipalmitoyloxy-propyl]-N-palmitoyl-(R)-cysteine ($Pam_3Cys$) (Spohn et al., Vaccine 2004, 22, 2494-2499; Metzger et al., J. Med. Chem. 1991, 34, 1969-1974) can elicit IgG antibody responses. This finding was significant because it had been difficult to elicit relevant immune responses against tumor-associated carbohydrates (Kuduk et al., J.Am.Chem.Soc. 1998, 120, 12474-12485; Danishefsky et al., Angew.Chem. Int. Ed. 2000, 39, 836-863).

To optimize the immunological properties of a three-component vaccine, a synthetic methodology was required, which would allow a convenient assembly of a number of B- and T-epitopes and lipopeptide adjuvants into a range of vaccine candidates. During our investigation, we discovered that liposome-mediated native chemical ligation (NCL) is a useful approach that greatly increases the reaction rates and yields of ligations of sparingly soluble peptide reactants (Ingale et al., Org Lett. 2006 Dec. 7; 8(25):5785-8; supplementary information is available electronically on the worldwide web at http://pubs.acs.org/subscribe/journals/orlef7/suppinfo/ol062423x/ol062423xsi20061107_021934.pdf). Importantly, for the first time the new approach makes it possible to employ lipidated peptides in NCL. The methodology is also attractive for NCL of lipophilic peptides, which usually give low yields of products under classical reaction conditions.

Compound 7, which is composed of the tumor-associated glycopeptide derived from MUC-1 (Snijdewint et al., Int. J. Cancer 2001, 93, 97-106) the well-documented T-cell epitope YAFKYARHANVGRNAFELFL (SEQ ID NO:2; YAF), and the lipopeptide $Pam_3CysSK_4$, was selected as a synthetic target. It was envisaged that this compound could be prepared from building blocks 2, 3, and 6 by sequential NCL. Thus, NCL between the cysteine moiety of 3 and the thioester of 2 should link the B- and T-epitopes. Next, removal of the S-acetamidomethyl (Acm) protecting group (Veber et al., J. Am. Chem. Soc. 1972, 94, 5456-5461) of the N-terminal cysteine of the ligation product should reveal a free cysteine thiol, which can then be ligated with the thioester of 6 to give required adduct 7.

MUC-1 epitope 3 was assembled by automated solid-phase peptide synthesis (SPPS) using Fmoc protected amino acids and $N^{\alpha}$FmocThr($\alpha$-$AcO_3$-D-GalNAc)OH (Tn antigen; Cato et al., J. Carb. Chem. 2005, 24, 503-516) on a Rink amide linker resin. After the assembly, the glycopeptide was cleaved from the solid support by treatment with TFA (94.0%), water (2.5%), ethanedithiol (2.5%) and TIS (1%). Next, the acetyl esters of the saccharide moiety were cleaved by treatment of 5% aqueous hydro-azine in the presence of DTT to give glycopeptide 3.

Peptide thioester 2 was synthesized on a sulfonamide "safety-catch" linker (Kenner et al., J. Chem. Soc. D-Chem. Commun. 1971, 636; Shin et al., J. Am. Chem. Soc. 1999, 121, 11684-11689; Ingenito et al., J. Am. Chem. Soc. 1999, 121, 11369-11374). Cleavage of the fully assembled peptide from the resin was accomplished by a two-step procedure entailing alkylation of the sulfonamide with iodoacetonitrile followed by treatment with benzyl mercaptan to give a protected peptide having a C-terminal thioester. The acid sensitive protecting groups of the peptide were removed by treatment with reagent B (TFA, phenol, water and TIS; 88/5/5/2) to give 2. This compound is equipped with an N-terminal cysteine residue carrying the orthogonal Acm thiol protecting group, which is stable under conventional side-chain deprotection with TFA but can be cleaved using Hg(II) or Ag(I), or oxidatively by using $I_2$. Finally, $Pam_3CysSK_4$ α-thioester 6 was synthesized similar to the preparation of compound 2.

Figure 4:
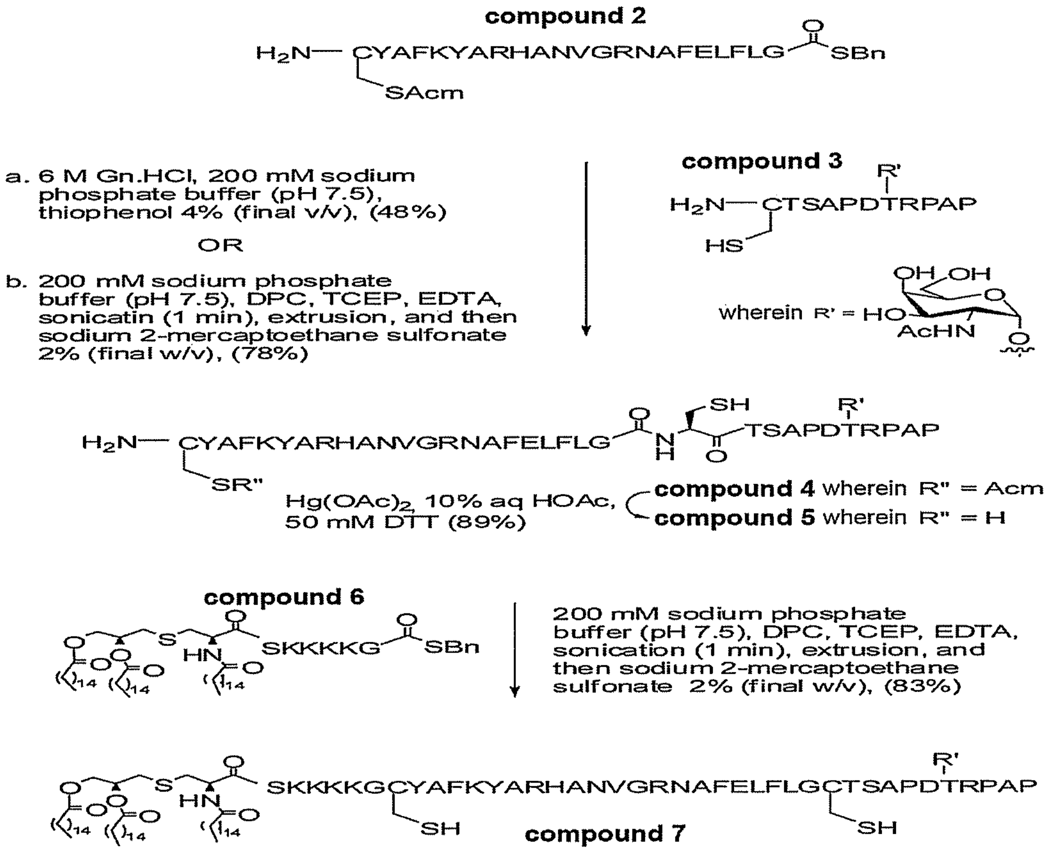
FIG. 4 shows synthesis of an exemplary three-component glycolipopeptide vaccine 7 using native chemical ligation (NCL) (Scheme 1).

Having building blocks 2, 3, and 6 at hand, attention was focused on the preparation of glycolipopeptide 7 by sequential NCL (Scheme 1, FIG. 4). The ligation of 2 with 3 was performed under standard conditions using a phosphate buffer (pH 7.5) containing 6 M of guanidinium-hydrochloride. The ligation was catalyzed by the addition of 4% thiophenol (v/v) (Dawson et al., J. Am. Chem. Soc. 1997, 119, 4325-4329) and the progress of the reaction monitored by LC/MS. The reaction was rather sluggish and after a reaction time of 18 hours partial conversion of 2 and 3 into 4 and some hydrolysis of the thioester was observed. Purification by semi-preparative RP-HPLC gave 4 in a yield of 48%. Next, the Acm group of 4 was removed using mercury(II) acetate to give glycopeptide 5, containing a free sulfhydryl moiety. Unfortunately, a second NCL of compound 5 with the thioester 6 in a phosphate buffer containing 6 M guanidinium-hydrochloride and thiophenol did not provide target compound 7. The failure of this reaction is probably due to the poor solubility of 6. Addition of detergents Such as SDS (Valiyaveetil et al., J. Am. Chem. Soc. 2002, 124, 9113-9120) and DPC (Clayton et al., Proc. Natl. Acad. Sci. U.S.A. 2004, 101, 4764-4769), at ambient and elevated reaction temperatures (40-50° C.) did not improve the ligation. Furthermore, the use of alternative catalysts such as a mixture of sodium thiophenate and thiopheniol or sodium 2-mercaptoethane sulfonate did not lead to product formation. Attempts to perform the ligation in a phosphate buffer containing 8 M urea and use of trifluoroethanol as a reaction solvent also led to failure.

We envisaged that the incorporation of compounds 5 and 6 into liposomes would facilitate solubilization (Hunter et al., Bioconj. Chem. 2004, 15, 437-440; Otaka et al., Chem. Commun. 2004, 1722-1723) and hence increase the rate of ligation. Thus, a film of dodecylphosphocholine, thiol 5, and thioester 6 was hydrated by incubation at 37° C. for 4 hours in a phosphate buffer (pH 7.5) in the presence of carboxyethyl phosphine and EDTA. The latter two reagents were added to suppress disulfide formation. The mixture was ultra-sonicated for 1 minute and the resulting vesicles were sized to 1 μm by passing through a polycarbonate membrane filter. The ligation was catalyzed by the addition of sodium 2-mercaptoethane sulfonate (Grogan et al., J. Am. Chem. Soc. 2005, 127, 14383-14387) and, surprisingly, after a reaction time of 2 hours, LC-MS showed completion of the reaction. After purification by RP-HPLC over a C-4 column, compound 7 was obtained in a high yield of 83%. The use of thiophenol as a catalyst resulted in a significantly slower reaction rate and after 4 hours the reaction had proceeded to only ~60% completion. After a reaction time of 16 hours, LC-MS revealed significant hydrolysis of palmitoyl esters.

Encouraged by the successful preparation of 7, attention was again on the synthesis of glycopeptide 4 this time using the new methodology. The preparation of this compound by traditional NCL was relatively low yielding due to the poor solubility of 2 in a phosphate buffer containing 6 M guanidinium-hydrochloride. It was envisaged that incorporation of 2 and 3 into liposomes would increase the solubility and hence a higher yield of product may be expected. Thus, a liposomal preparation of peptide 2 and glycopeptide 3 was prepared using the conditions employed for the preparation of 7. The ligation was catalyzed by the addition of sodium 2-mercaptoethane sulfonate and, after a reaction time of 2 hours, the product was purified by RP-HPLC to give 4 in an excellent yield of 78%.

Interestingly, no product formation was observed when a solution of 3 was added to a liposomal preparation of 2 using sodium 2-mercaptoethane sulfonate as the promoter (compound 3 has reasonable solubility in phosphate buffer). The results of these experiments indicate that NCL takes place within the lipid environment of the liposome and not at the water-liposome interface.

Figure 5:
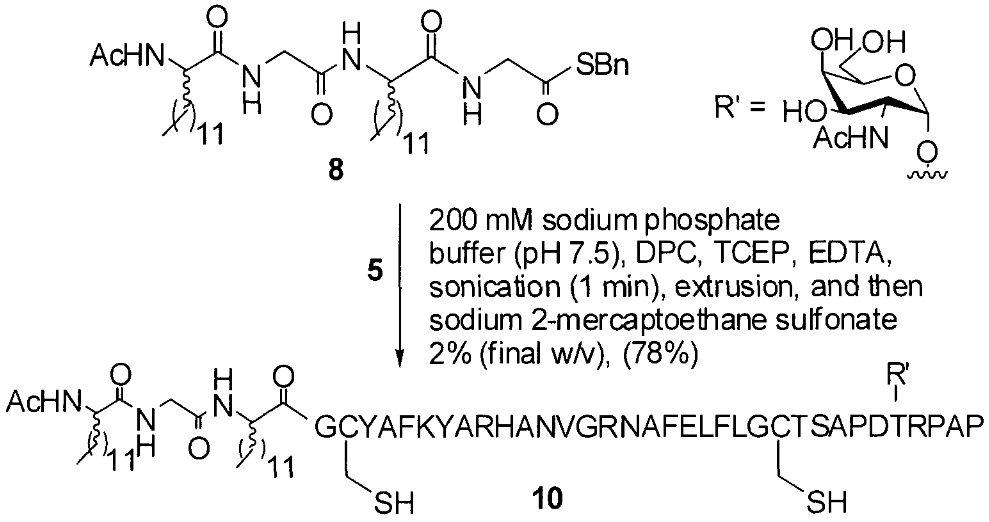
FIG. 5 shows preparation of 10 from 5 and 8 (Scheme 2).
Figure 6:
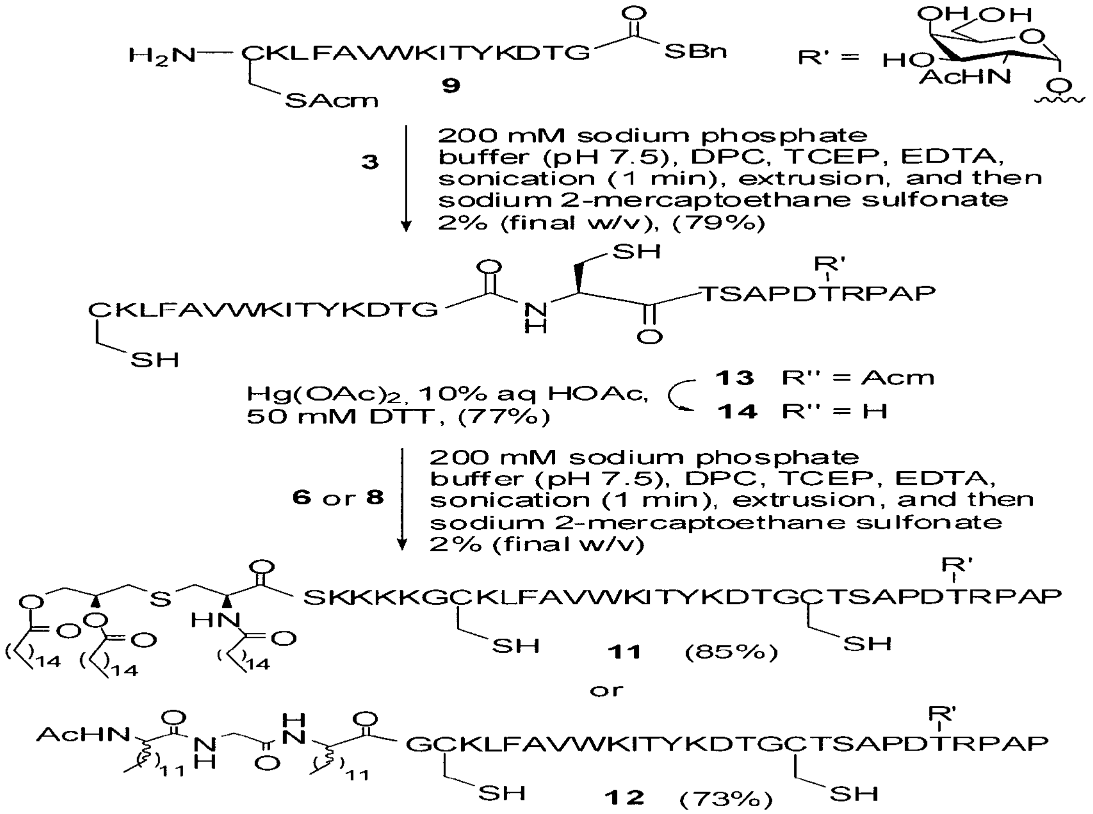
FIG. 6 shows preparation of 11 and 12 from 3, 6, 8 and 9 (Scheme 3).

To examine the utility of the approach, compounds 10 (Scheme 2; FIG. 5), 11, and 12 (Scheme 3; FIG. 6), which differ in (glyco)peptide and lipid composition, were prepared by sequential liposome-mediated NCL starting from building blocks 2, 3, 6, 8, and 9. Thus, glycolipopeptide 10 could easily be obtained by ligation of 5, which was prepared from compounds 2 and 3 with thioester-8. Derivatives 11 and 12 were prepared by ligation of 3 with 9 to give glycopeptide 13, which after removal of the Acm group (→14) was ligated with thioesters 6 or 8, respectively. In each liposome-mediated NCL the thioester was consumed within 2 hours as determined by LC-MS, and after purification by semi-preparative RP-HPLC the glycopeptides or glycolipopeptides were obtained in high yield.

Previously, Kochendoerfer and co-workers (Hunter et al., Bioconj. Chem. 2004, 15, 437-440) performed a NCL between a synthetic hydrophobic polypeptide incorporated into a cubic lipidic phase and a tetrapeptide, which was added to the membrane preparation. This mode of ligation is different from the approach described here because only one of the two reactants is incorporated into the membrane. Furthermore, Otaka and coworkers (Otaka et al., Chem. Commun. 2004, 1722-1723) reported that lipid bilayer assisted NCL between a thioester and an N-terminal cysteine peptide can successfully be used for the synthesis of membrane protein segments possessing two transmembrane regions and one extracellular domain. In this approach, peptides were embedded in a palmitoyloleoyl phosphatidylcholine membrane and the reaction was catalyzed by the addition of thiophenol.

The results of our study demonstrate that incorporation of a lipophilic (lipo)peptide thioester and an N-terminal cysteine glycopeptide into DPC-liposomes facilitates NCL to afford a range of glycopeptides and glycolipopeptides. Surprisingly, the new approach is not limited to peptides that have a trans- and an extra cellular domain. Furthermore, it was found that 2-mercaptoethane sulfonate is a more effective catalyst compared to thiophenol. In this respect, it was observed that the liposome-mediated NCLs were completed within 2 hours, which is remarkably fast for the type of substrates employed. The high reaction rate can probably be attributed to a concentration effect in the liposomes.

In conclusion, we have developed a novel approach for native chemical ligation by the entrapment of reactants in liposomes. The new methodology is particularly suited for the synthesis of lipophilic (glyco)peptides of biological importance (Guo et al., Med. Res. Rev. 2005, 25, 655-678; Buskas et al., Glycobiology, 2006, 16, 113R-136R; Dube et al., Nat. Rev. Drug Disc. 2005, 4, 477-488; Doores et al., Chem. Eur. J. 2006, 12, 656-665; Macmillan et al., Angew. Chem. Int. Ed. 2004, 43, 1355-1359; Dziadek et al., Angew. Chem. Int. Ed. 2005, 44, 7624-7630). For example, it allows the synthesis of a range of three-component vaccine candidates by a modular approach using an array of B- and T-epitopes and lipopeptide adjuvants. A modular approach is attractive because it provides greater synthetic flexibility than linear synthesis. In this respect, each building block can be used for the preparation of several different target compounds. Furthermore, compared to conventional linear SPPS, a block synthetic approach will minimize by-product build-up in the growing peptide chain. In this respect, the DT sequence of the MUC-1 glycopeptide is prone to aspartimide formation (Mergler et al., J. Pept. Sci. 2003, 9, 518-526) which can occur at each coupling step. In a convergent block synthesis, the individual building blocks can be purified by RP-HPLC and characterized by NMR and MS prior to assembly, providing a sound basis for highly pure final products.

Materials and Methods

Reagents and general experimental procedures: Amino acid derivatives and resins were purchased from NovaBioChem and Applied Biosystems; DMF from EM Science; and NMP from Applied Biosystems. Dodecyl phosphocholine was obtained from Avanti Polar Lipids. All other chemical reagents were purchased form Aldrich, Acros, Alfa Aesar and Fischer and used without further purification. All solvents employed were reagent grade. Reverse Phase HPLC was performed on an Agilent 1100 series system equipped with an autosampler, UV-detector and fraction-collector. RP-HPLC was carried out by using a Zorbax Eclipse C8 analytical column (5 μm, 4.6×150 mm) at a flow rate of 1 ml/m, a semi-preparative C8 column (5 μm, 25×250 mill) at a flow rate of 4 ml/mm, a Synchropak C4 analytical column (5 μm, 4.6×100 mill) at a flow rate of 1 ml/mm and a Vydac C4 semi preparative column (5 μm, 4.6×250 mill) at a flow rate of 2 ml/min. All runs used linear (gradients of 0-95% solvent B in A over a 40 min. period unless otherwise specified. (A=0.1% TFA in water, B=0.1% TFA in acetonitrile). MALDI-ToF mass spectra were recorded on a ABI 4700 proteomic analyzer.

General methods for Solid-Phase Peptide Synthesis (SPPS): Peptides were synthesized by established protocols on a Applied Biosystems, ABI 433A peptide synthesizer equipped with UV-detector using $N^{\alpha}$-Fmoc-protected amino acids and 2-(1H-benzotriazole-1-yl)-oxy-1,1,3,3-tetramethyl hexafluorophosphate (HBTU)/1-Hydroxybenzotriazole (HOBt) as the activating reagents. Single coupling steps were performed with conditional capping. The coupling of the glycosylated amino acid $N^{\alpha}$-Fmoc-Thr-($Ac_3$-α-D-GalNAc) and N-Fmoc-R-(2,3-bis(palmitoyloxy)-(2R-propyl)-(R)-cysteine were carried out manually. The manual couplings were monitored by standard Kaiser test.

Figure 7:
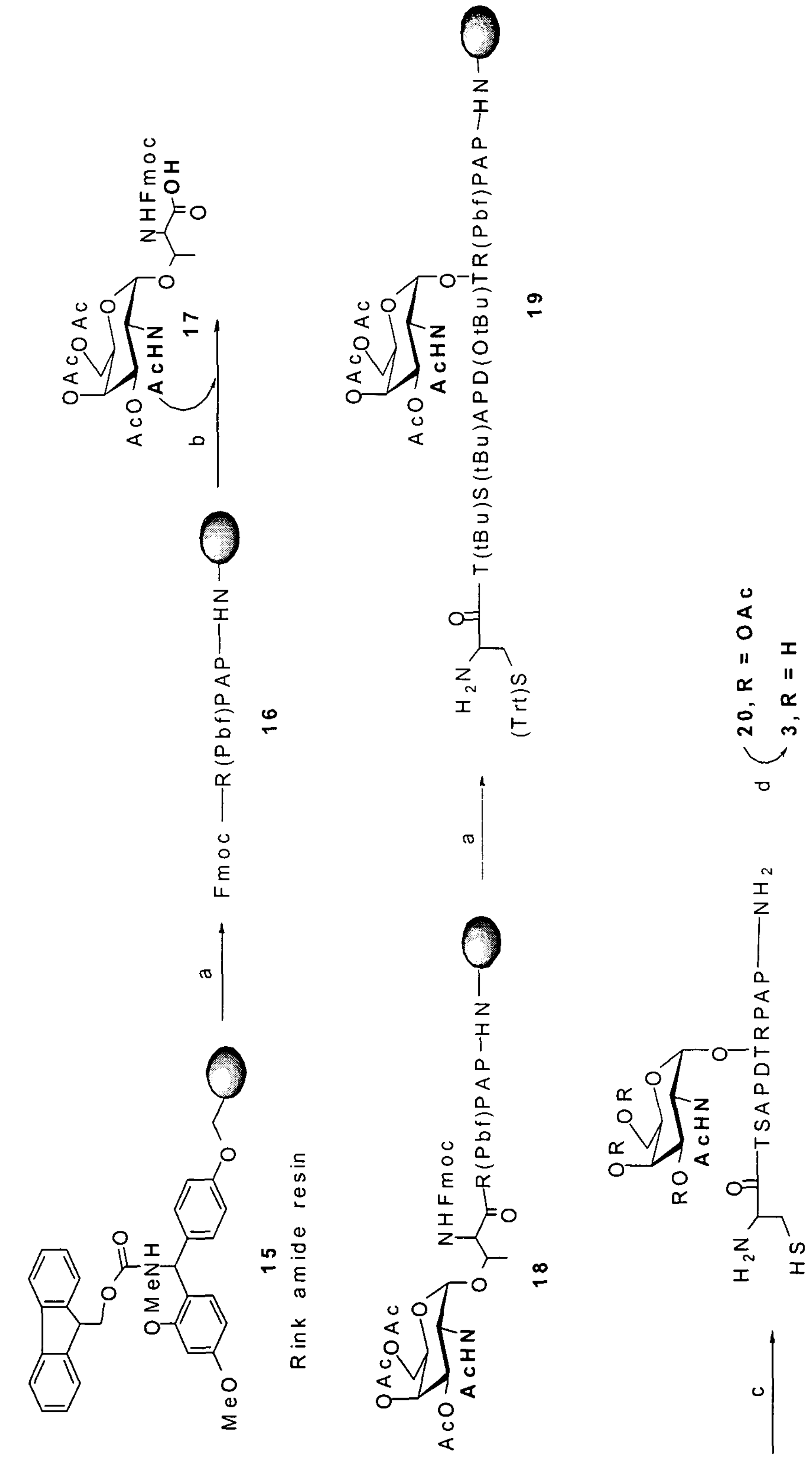
FIG. 7 shows synthesis of cys-glycopeptide 3; (a) SPPS using Fmoc-chemistry, coupling with HBTU/HOBt (Knorr et al., Tetrahedron. Lett. 1989, 30, 1927-1930) in the presence of DIPEA in NMP; (b) 17', HATU/HOAt, DIPEA, DMF, overnight; (c) TFA (94.0%), water (2.5%), EDT (2.5%), TIS (1%); (d) 5% aqueous hydrazine, excess of DTT (Scheme 4).

Synthesis of Cys-MUC1 glycopeptide (20): The synthesis of Cys-glycopeptide (3) is shown in Scheme 4 (FIG. 7). SPPS was performed on a Rink amide linker resin (0.1 mmol) as described above. Side chain protection was as follows: $N^{\alpha}$-Fmoc-Arg (2,2,4,6,7-pentamethyldihydrobenzofuran-5-sulfonyl), $N^{\alpha}$-Fmoc-Asp(O-tert-butyl), $N^{\alpha}$-Fmoc-Cys(Trt), $N^{\alpha}$-Fmoc-Ser(tert.-butyl), $N^{\alpha}$-Fmoc-Thr(tert.-butyl). The first four amino acids, Arg-Pro-Ala-Pro were coupled on the peptide synthesizer using a standard protocol. After the completion of the synthesis, a manual coupling was carried out using $N^{\alpha}$-Fmoc-Thr-($AcO_3$-α-D-GalNAc) (0.4 mmol, 268 mg), with PyBOP (0.4 mmol, 208 mg), HOBt (0.4 mmol, 55 mg) and DIPEA (0.4 mmol, 70 μl) in DMF for 12 hrs. The coupling reaction was monitored by standard Kaiser test. The resin was washed with DMF (6 ml) and DCM (6 ml), and resubjected to the same coupling conditions to ensure complete coupling. The glycopeptide was then elongated on peptide synthesizer. The resin was thoroughly washed with DMF (6 ml), DCM (6 ml) and MeOH (6 ml) and dried in vacuo to constant weight. The resin was then swelled in DCM (5 ml) for 1 hr. After which it was treated with 94% TFA, 2.5% water, 2.5% EDT and 1% TIS (10 ml) for 2 hr at room temperature. The resin was filtered and washed with neat TFA (2 ml). The filtrate was then concentrated in vacuo approximately ⅓ of its original volume. The peptide was then precipitated using diethyl ether (0° C.) and recovered by centrifugation at 3000 rpm for 15 min. The crude glycopeptide was purified by RP-HPLC on a semi-preparative C-18 reversed phase column using a linear gradient of 0-95% solvent B in A over a period of 40 min., and lyophilization of the appropriate fractions afforded 20 (90% based on resin loading capacity). MALDI-ToF MS: observed, 1443.8918 Da; calculated, 1443.5371 Da.

Deacetylation of Cys-MUC1-glycopeptide (3): The glycopeptide 20 (5 mg, 3.4 μmol) was treated with 5% aqueous hydrazine (2 ml) containing excess of DTT (12 mg), the reaction was monitored by MALDI-ToF MS. After standing for 1 hr at room temperature, the crude product was purified by RP-HPLC on a semi-preparative C-18 reversed phase column using a linear gradient of 0-95% solvent B in A over a period of 40 min., to afford after lyophilization compound 3 (4.0 mg, 88%). MALDI-ToF MS: observed, 1317.9580 Da; calculated, 1317.4271 Da.

Figure 8:
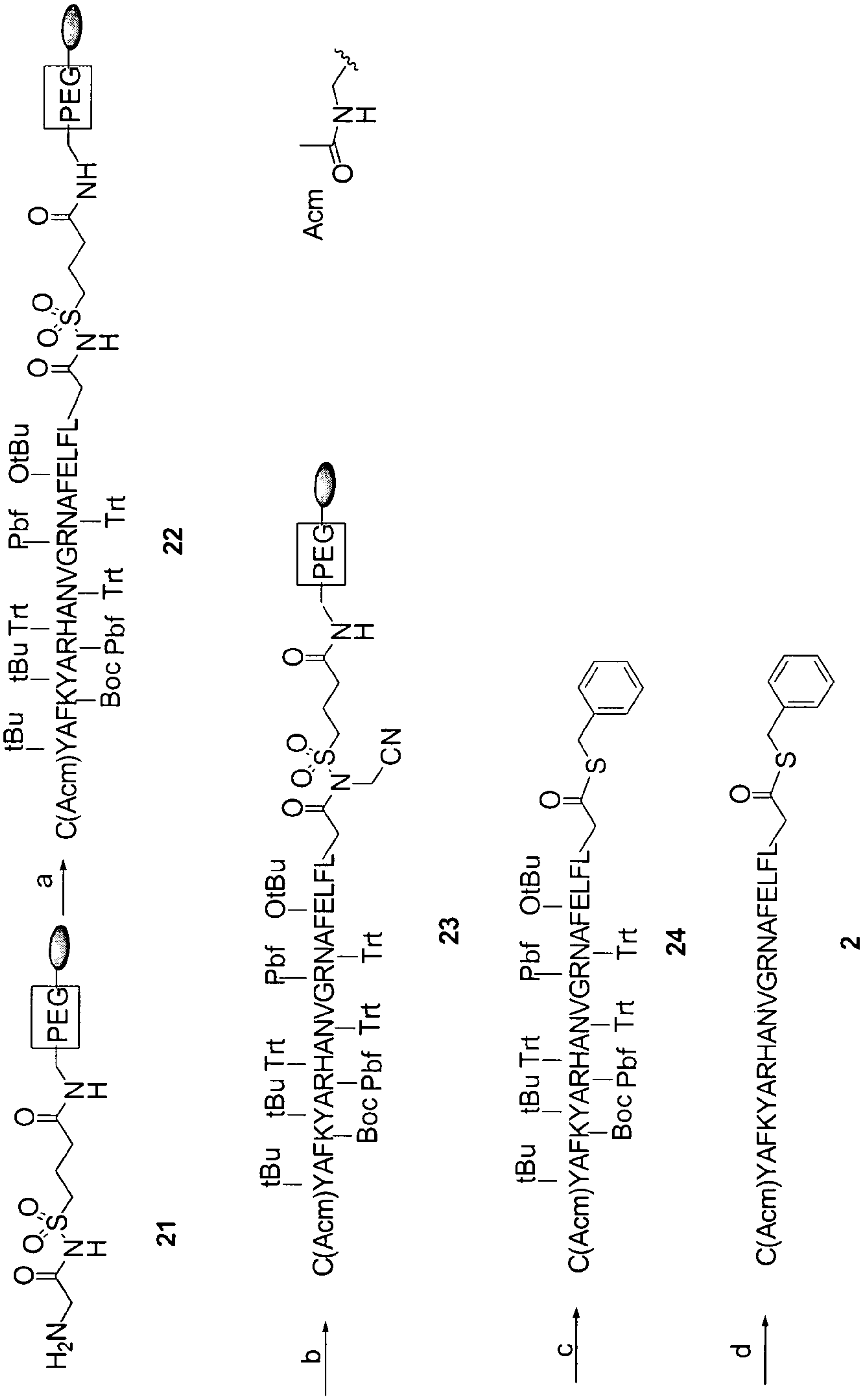
FIG. 8 shows synthesis of cys(Acm)-$^{\alpha}$thioester peptide 2 using the alkanesulfonamide “safety-catch” linker. (a) SPPS using Fmoc-chemistry, coupling with HBTU/HOBt in the presence of DIPEA in NMP; (b) $ICH_2CN$, DIPEA, NMP, 24 hr; (c) BnSH, Na-Thiophenate,THF, 24 hr; (d) Reagent B (TFA (88%), Phenol (5%), $H_2O$ (5%), TIS (2%)), 4 hr (Scheme 5).

Synthesis of C (Acm)YAFKYARHANVGRNAFELFLG-COSBn (2): The synthesis of Cys(Acm)-thioester peptide (2) is shown in Scheme 5 (FIG. 8). The synthesis of Acm protected peptide thioester was carried out on preloaded H-Gly-sulfamylbutyryl Novasyn TG resin (0.1 mmol) as described in the general methods section for peptide synthesis. The following side chain protection was employed: $N^{\alpha}$-Fmoc-Arg(2,2,4,6,7-pentamethyldihydrobenzofuran-5-sulfonyl), $N^{\alpha}$-Fmoc-Asn(Trt), $N^{\alpha}$-Fmoc-Cys(Acm), $N^{\alpha}$-Glu(O-tert.-butyl), Glu(O-tert.-butyl), $N^{\alpha}$-His(Trt), $N^{\alpha}$-Fmoc-Lys(Boc), $N^{\alpha}$-Fmoc-Thr(tert.-butyl), $N^{\alpha}$-Fmoc-Tyr(tert.-butyl).

Activation and cleavage. The resin bound peptide was washed thoroughly with DCM (10 ml) and N-methyl-2-pyrrolidone (NMP) until the swelling was complete (1 hr). The resin was then treated with DIPEA (0.5 ml, 3 mmol), iodoacetonitrile (0.36 ml, 5 mmol) in NMP (6 ml). Before addition, iodoacetonitrile (0.36 ml) was filtered through a plug of basic alumina. The resin was then agitated under the exclusion of light for 24 hrs, filtered and then washed with NMP (20 ml), DCM (20 ml) and THF (20 ml). The activated N-acyl sulfonamide resin was swollen in DCM (5 ml), drained and then transferred to a 50 ml round bottom flask. To the resin-containing flask was added THF (4 ml) and benzyl mercaptan (0.64 ml, 5 mmol), and sodium thiophenate (27 mg, 0.2 mmol). After agitation for 24 hrs, the resin was filtered and washed with DMF (3 ml). The combined filtrate and washings were collected and concentrated in vacuo. The crude peptide was triturated with tert-butyl methyl ether (0° C.) (60 ml).

Side chain deprotection: The protected peptide was treated with of reagent B (5 ml, (TFA 88%, phenol 5%, $H_2O$ 5%, TIS 2%)) for 6 hrs at room temperature. The TFA solution was then added drop wise to a screw cap centrifuge tube containing ice cold tert-butyl methyl ether (40 ml) and the resulting suspension was left overnight at 4° C., after which the precipitate was collected by centrifugation at 3000 rpm (20 min), and after the decanting of the ether the peptide precipitate was resuspended in ice cold tert-butyl methyl ether (40 ml) and the process of washing was repeated twice. The crude peptide was purified by semi preparative C-8 reversed phase column using a linear gradient of 0-95% solvent B in A over a period of 40 min., and lyophilization of the appropriate fractions afforded 2 in good yield (79% based on resin loading capacity). MALDI-ToF MS: observed, [M+Na] 2748.2439 Da; calculated, [M+Na] 2748.1584 Da.

Figure 9:
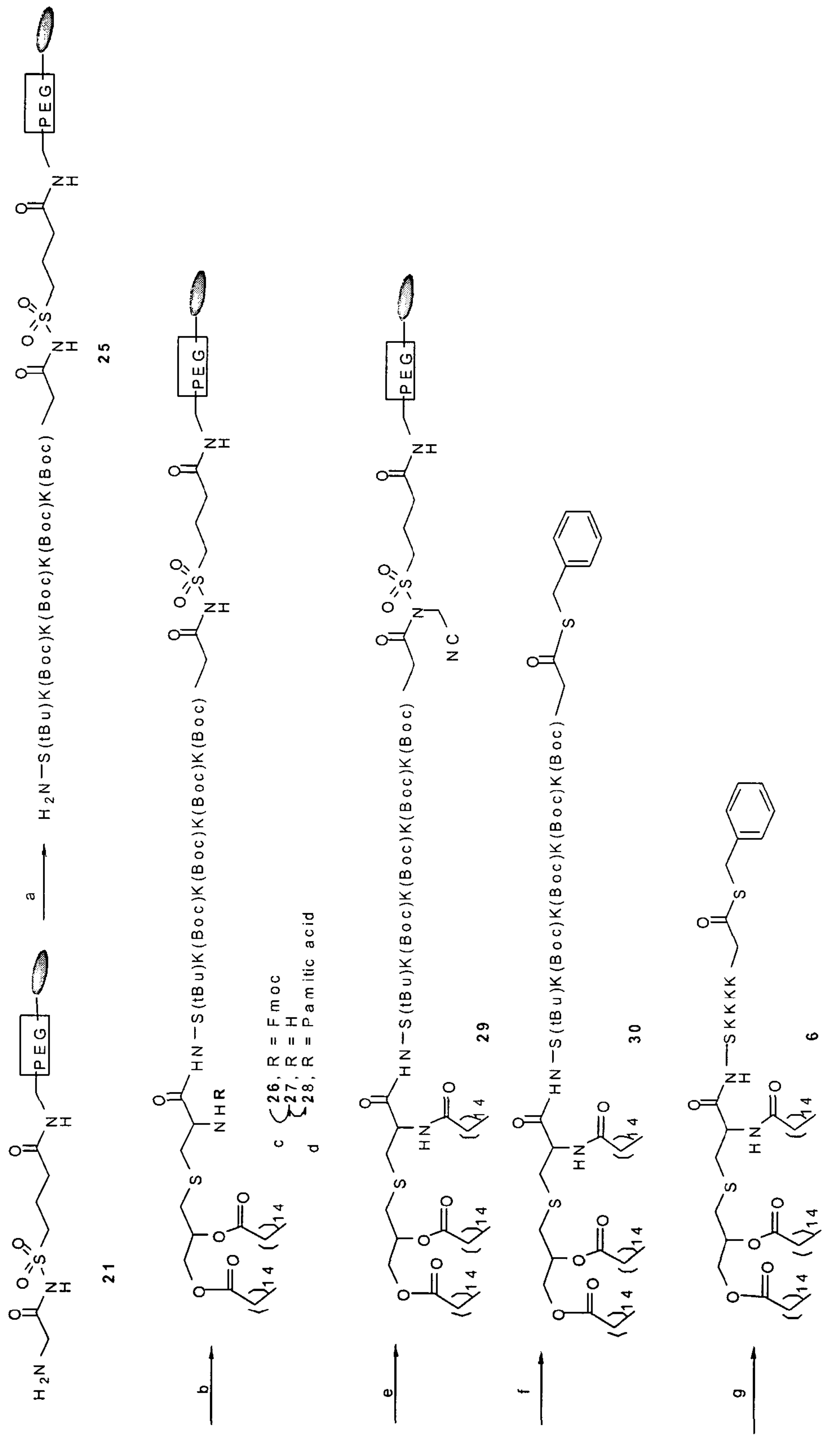
FIG. 9 shows synthesis of lipopeptide $^{\alpha}$thioester 6 using the alkanesulfonamide “safety-catch” linker. (a) SPPS using Fmoc-chemistry, coupling with HBTU/HOBt in the presence of DIPEA in NMP; (b) Manual coupling of $Pam_2Cys$-OH (Metzger et al., Int. J. Pro. Pep. Res. 1991, 38, 545-554), PyBOP, HOBt in the presence of DIPEA in DMF; (c) 20% Piperidine in DMF; (d) Coupling of Palmitic acid, PyBOP, HOBt in the presence of DIPEA in DMF; (e) $ICH_2CN$, DIPEA, NMP, 24 hr; (f) BnSH, Na-Thiophenate,THF, 24 hr; (g) Reagent B (TFA (88%), Phenol (5%), $H_2O$ (5%), TIS (2%)), 4 hr (Scheme 6).

Synthesis of lipopeptide thioester (6). The chemical synthesis of lipopeptide thioester (6) is shown in Scheme 6 (FIG. 9). The synthesis of 6 was carried out on a H-Gly-sulfamylbutyryl Novasyn TG resin (0.1 mmol) as described in the general methods. After coupling of the first five amino acids, the remaining steps were performed manually. N-Fmoc-R-(2,3-bis(palmitoyloxy)-(2R-propyl)-(R)-cysteine (267 mg, 0.3 mmol) was dissolved in DMF (5 ml) and PyBOP (156.12 mg, 0.3 mmol), HOBt (40 mg, 0.3 mmol) and DIPEA (67 μl, 0.4 mmol) were added. After premixing for 2 min, the mixture was added to the resin. The coupling reaction was monitored by the Kaiser test. Upon completion of the coupling, the N-Fmoc group was cleaved using 20% piperidine in DMF (6 ml). Palmitic acid (77 mg, 0.3 mmol) was coupled to the free amine as described above using PyBOP (156.12 mg, 0.3 mmol), HOBt (40 mg, 0.3 mmol) and DIPEA (67 μl, 0.4 mmol) in DMF. The resin was thoroughly washed with DMF (10 ml), DCM (10 ml) and MeOH (10 ml) and then dried in vacuo. Side chain deprotection was carried out by using the method described for peptide 2. The crude peptide was purified by HPLC on a semi preparative C-4 reversed phase column using a linear gradient of 0-95% solvent B in A over a 40 mm., and the appropriate fi-actions were lyophilized to afford 6 (65% based on resin loading capacity). MALDI-ToF MS: observed, [M+Na] 1695.2335 Da; calculated, [M+Na] 1695.4714 Da.

Figure 10:
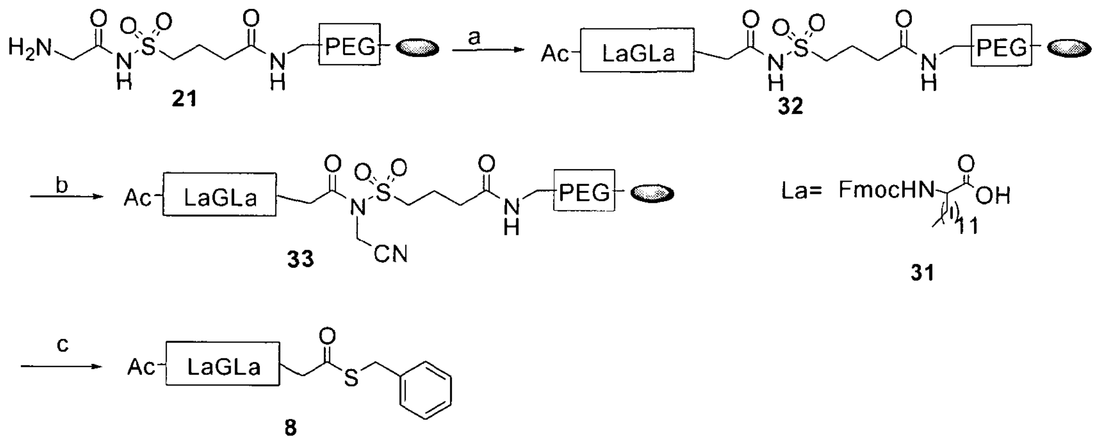
FIG. 10 shows synthesis of lipidated amino acid $^{\alpha}$ thioester 8 using the alkanesulfonamide “safety-catch” linker. (a) i. Manual coupling of Fmoc-lipidated amino acid with PyBOP/HOBt in the presence of DIPEA in DMF; ii. 20% Piperidine in DMF; iii. Manual Coupling of Fmoc-Gly-OH with PyBOP/HOBt in the presence of DIPEA in DMF; iv. 20% Piperidine in DMF; v. Manual coupling of Fmoc-lipidated amino acid (Gibbons et al. Liebigs Ann. Chem. 1990, 1175-1183; Koppitz et al., Hely. Chim. Acta. 1997, 80, 1280-1300) with PyBOP/HOBt in the presence of DIPEA in DMF; vi. 20% Piperidine in DMF; vii. 10% $Ac_2O$, 5% DIPEA in NMP for 10 min; (b) $ICH_2CN$, DIPEA, NMP, 24 hr; (c) BnSH, Na-Thiophenate,THF, 24 hr (Scheme 7).

Synthesis of lipopeptide thioester (8). The chemical synthesis of lipidated amino acid thioester (8) is shown in Scheme 7 (FIG. 10). The synthesis of 8 was carried out on a H-Gly-sulfamylbutyryl Novasyn TG resin (0.1 mmol) by a manual procedure. N-α-Fmoc-Gly-OH (90 mg, 0.3 mmol) was dissolved in DMF (5 ml) and PyBOP (156.12 mg, 0.3 mmol), HOBt (40 mg, 0.3 mmol) and DIPEA (67 μl, 0.4 mmol) were added. After standing for 2 min, the mixture was added to the resin. The coupling reaction was monitored by Kaiser test. Upon completion of the coupling, the N-Fmoc group was cleaved using 20% piperidine in DMF (6 ml). N-α-Fmoc-Lipidated amino acid 31 (139.57 mg, 0.3 mmol) was coupled to the free amine of the resulting product as described above using PyBOP (156.12 mg, 0.3 mmol), HOBt (40 mg, 0.3 mmol) and DIPEA (67 μl, 0.4 mmol) in DMF. This cycle was repeated twice. Finally, the N-Fmoc group was cleaved using 20% piperidine in DMF (6 ml) and acetylated using 5 ml of 10% $Ac_2O$, 5% DIPEA in NMP for 10 min. The resin was thoroughly washed with DMF (10 ml), DCM (10 ml) and MeOH (10 ml) and dried in vacuo. The product was cleaved from the resin by using the method described for peptide 2. The crude peptide was purified by HPLC on a semi preparative C-4 reversed phase column using a linear gradient of 0-95% solvent B in A over a period of 40 min., and the appropriate fractions were lyophilized to afford 8 (69% based on resin loading capacity). MALDI-ToF MS: observed, [M+Na] 753.4871 Da; calculated, [M+Na] 753.5067 Da.

Figure 12:
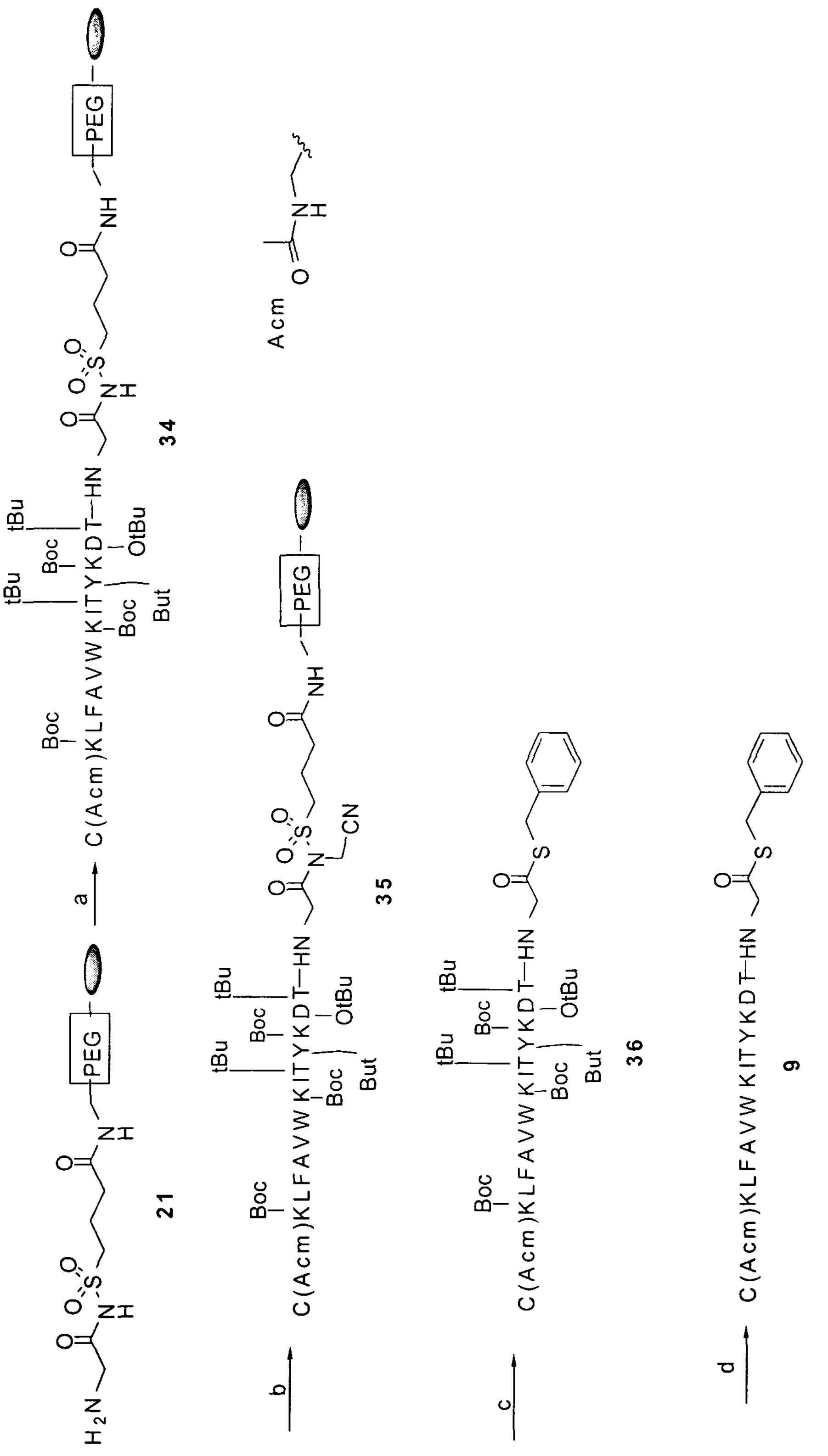
FIG. 12 shows synthesis of Cys(Acm)-$^{\alpha}$thioester 9 using the alkanesulfonamide “safety-catch” linker. (a) SPPS using Fmoc-chemistry, coupling with HBTU/HOBt in the presence of DIPEA in NMP; (b) $ICH_2CN$, DIPEA, NMP, 24 hr; (c) BnSH, Na-Thiophenate,THF, 24 hr; (d) Reagent B (TFA (88%), Phenol (5%), $H_2O$ (5%), TIS (2%)), 4 hr (Scheme 9).

Synthesis of C(Acm)KLFAVWKITYKDTGCOSBn (9): Cys (Acm)-T-epitope thioester (9) is shown in Scheme 9 (FIG. 12). The synthesis of Acm protected peptide thioester was carried out on preloaded H-Gly-sulfamylbutyryl Novasyn TG resin (0.1 mmol) as described in the general methods section for peptide synthesis. Side chain protection was as follows: $N^{\alpha}$-Fmoc-Asp(O-tert.-butyl), $N^{\alpha}$-Fmoc-Cys (Acm), $N^{\alpha}$-Fmoc-Lys(Boc), $N^{\alpha}$-Thr(tert.-butyl), $N^{\alpha}$-Fmoc-Tyr(tert.-butyl). Activation, cleavage and side chain deprotection was performed by the method described for compound 2. The crude peptide was purified by semi preparative C-8 reversed phase column using a linear gradient of 0-95% of solvent B over A over period of 40 min., and lyophilization of the appropriate fractions afforded 9 in good yield (74% based on resin loading capacity). MALDI-ToF MS: observed, [M+Na] 1972.1240 Da; calculated, [M+Na] 1973.3716 Da.

Ligation between 2 and 3 to give 5. Method A. The peptide thioester 2 (10 mg, 3.6 μmol) and peptide 3 (7.24 mg, 5.5 μmol) were dissolved in 6 M Gn.HCl, 200 mM sodium phosphate (pH 7.5) as 1:1.5 ratios to obtain final concentration of 1 mM. The ligation was started by the addition of 4% thiophenol (300 μl). The ligation reaction was carried out in an incubator at 37° C. and the progress of the reaction was periodically monitored by RP-HPLC and LC-MS. After a reaction time of 18 hrs, the reaction was diluted with 2-mercaptoethanol in ligation buffer (3 ml). The resulting mixture was then purified by C-8 semi-preparative reversed phase column using linear gradients of 0-95% solvent B in A over 40 min., and the appropriate fractions were collected and lyophilized to give 4 (6.7 mg, 48%). The Acm protecting group of the ligated product was removed by dissolving the glycopeptide in 10% aq. AcOH (2 ml) (pH 4.0) followed by the treatment of Hg (II) acetate (8.18 mg) for 30 min., the reaction was quenched by addition of DTT (5.27 mg). The Acm deprotected product was purified by semi-preparative RP-HPLC using a water/acetonitrile gradient to yield 5 (5.7 mg, 87%). MALDI-ToF MS: observed, 3847.6615 Da, calculated, 3847.3031 Da.

Method B. The peptide thioester 2 (2 mg, 0.73 μmol) and peptide 3 (1.44 mg, 1.1 μmol), and dodecyl phosphocholine (1.5 mg, 4.4 μmol) were dissolved in a mixture of trifluoroethanol and $CHCl_3$ (2.5 ml/2.5 ml). The solvents were removed under reduced pressure to give a lipid/peptide film on the surface of the round bottom flask. The lipid/peptide film was hydrated for 4 hours at 37° C. using 200 mM phosphate buffer (pH 7.5, 2 ml) in the presence of tris(carboxyethyl)phosphine (2% w/v) and EDTA (0.1% w/v). The mixture was ultrasonicated for 1 min. The peptide/lipid suspension was extruded through 1.0 μm polycarbonate membranes (Whatman, Nucleopore, Track-Etch Membrane) at 50° C. to obtain uniform vesicles. To the vesicle suspension was added sodium 2-mercaptoethane sulfonate (2% w/v) to initiate the ligation reaction. The reaction was carried out in an incubator at 37° C. and was complete within 2 hours. The reaction was then diluted with 2-mercaptoethanol in ligation buffer (2 ml). The resulting mixture was purified by RP-HPLC on a semi-preparative C-8 reversed phase column using a linear gradient of 0-95% solvent B in A over a 40 min., and the fraction possessing the expected product as determined by MALDI-ToF were collected and lyophilized to give 4 (2.2 mg, 78%). The Acm protecting group of the ligated product was removed by dissolving the glycopeptide in 10% aq. AcOH (2 ml) (pH 4.0) followed by the treatment of Hg(II) acetate (2.7 mg) for 30 min., the reaction was quenched by addition of DTT (1.7 mg). The Acm deprotected product was purified by semi-preparative RP-HPLC using a water/acetonitrile gradient to yield 5 (1.9 mg, 89%). MALDI-ToF MS: observed, 3847.6015 Da, calculated, 3847.3031 Da.

Figure 11:
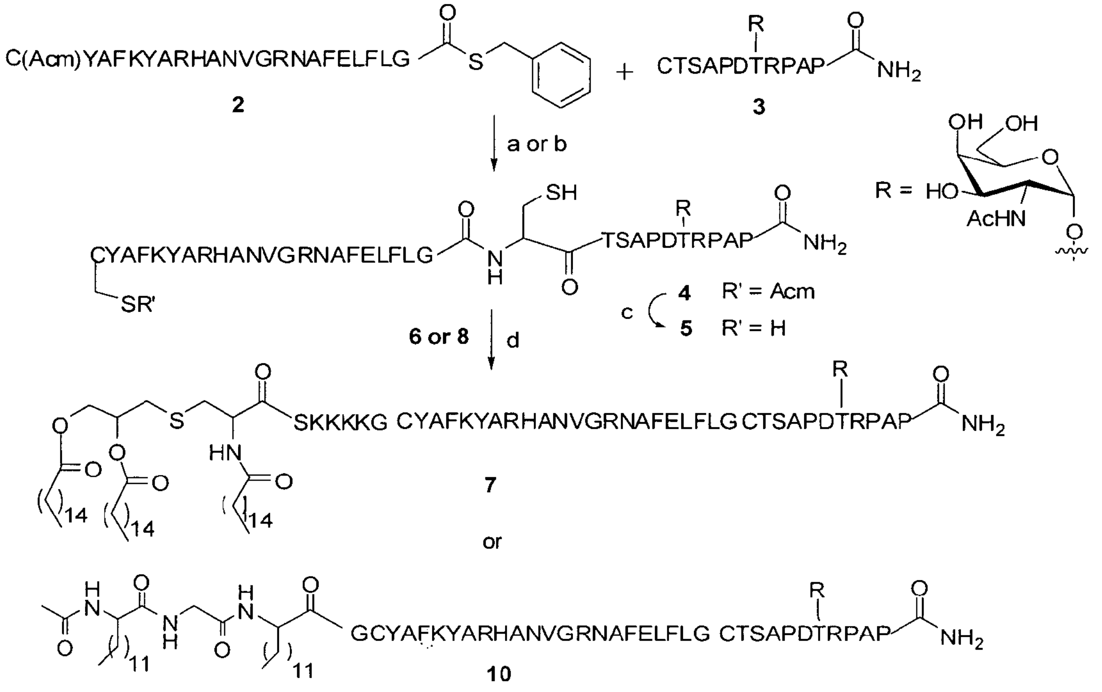
FIG. 11 shows sequential native chemical ligation of 7 or 10, (a) 6 M Gn-HCl, 200 mM sodium phosphate buffer (pH 7.5), thiophenol 4% (final v/v); (b) 200 mM Sodium Phosphate buffer, pH 7.5, DPC, tris(carboxyethyl)phosphine (2% w/v), EDTA (0.1% w/v), sonication (1 min), extrusion and then, Sodium 2-mercapto-ethanesulfonate (2% w/v); (c) $Hg(OAc)_2$, 10% aq HOAc, DTT (Scheme 8).

Sequential native chemical ligation (7 or 10) is shown in Scheme 8 (FIG. 11).

Ligation between 5 and 6 to give 7: The peptide 5 (3.0 mg, 0.77 μmol) and peptide thioester 6 (1.96 mg, 1.1 μmol) was subjected to ligation reaction conditions as described in method B. The progress of the reaction was periodically monitored by MALDI-ToF which showed that the reaction was complete within 2 hours. The crude peptide was purified by semi preparative C-4 reversed phase column using a linear gradient of 0-95% solvent B in A over a 40 min., and lyophilization of the appropriate fractions afforded 7 (3.5 mg, 83%). MALDI-ToF MS: observed, 5392.9712 Da, calculated, 5392.0171 Da.

Ligation between 5 and 8 to give 10: The peptide 5 (2 mg, 0.51 μmol) and peptide thioester 8 (0.53 mg, 0.72 μmol) was subjected to ligation reaction conditions as described in method B. The progress of the reaction was periodically monitored by MALDI-ToF which showed that the reaction was complete within 2 hours. The crude peptide was purified by semi preparative C-4 reversed phase column using a linear gradient of 0-95% solvent B in A over a 40 min., and lyophilization of the appropriate fractions afforded 10 (1.7 mg, 78%). MALDI-ToF MS: observed, 4454.0313 Da, calculated, 4454.1791 Da.

Ligation between 3 and 9 to give 14: The peptide 3 (5.6 mg, 4.3 μmol) and peptide thioester 9 (6.0 mg, 3.0 μmol) was subjected to ligation reaction conditions as described in method B. The progress of the reaction was periodically monitored by MALDI-ToF which showed that the most of conversion within 2 hours. The resulting reaction mixture was purified by using RP-HPLC on a semi-preparative C-8 reversed phase column using linear gradients of 0-95% solvent B in A over a 40 min., the fraction possessing the expected mass were collected and lyophilized to give 13 (7.4 mg, 79%). The Acm protecting group of the ligated product was removed by dissolving the glycopeptide in 10% aq. AcOH (2 ml) (pH 4.0) followed by the treatment of Hg(II) acetate (11.5 mg) for 30 min. After which the reaction was quenched by addition of DTT (7.4 mg). The Acm deprotected product was purified by semi-preparative RP-HPLC using a water/acetonitrile gradient to yield 14 (5.6 mg, 77%). MALDI-ToF MS: observed, 3073.7275 Da, calculated, 3072.5129 Da.

Figure 13:
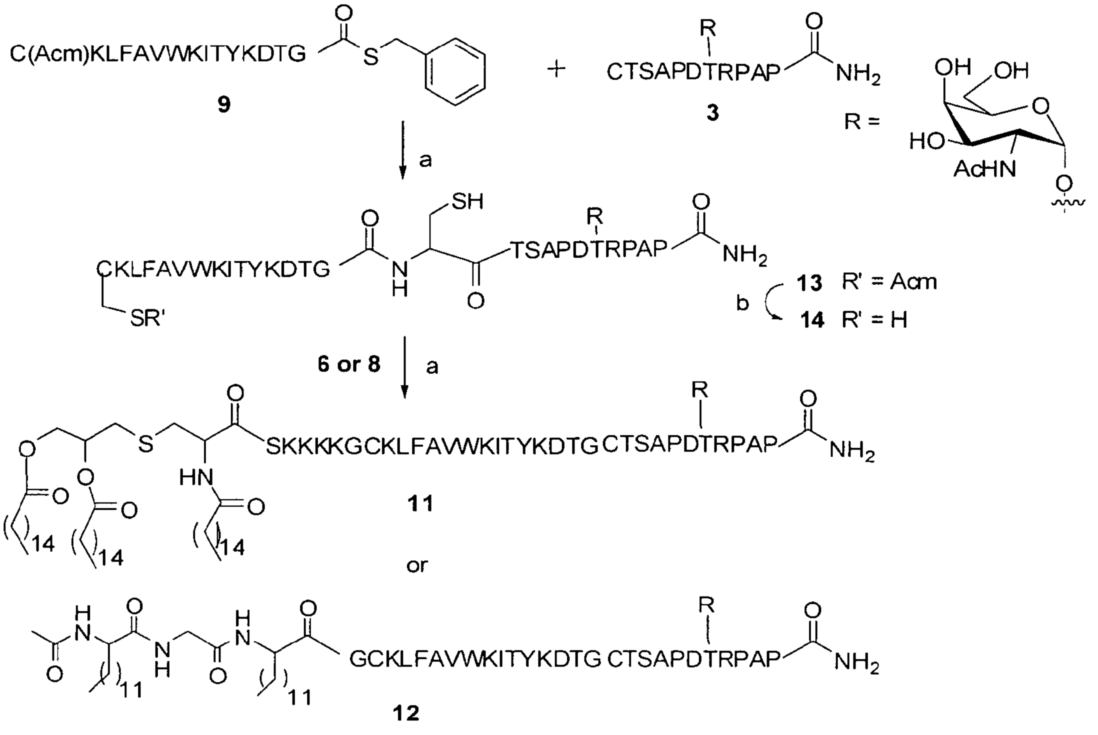
FIG. 13 Sequential native chemical ligation, (a) 200 mM Sodium Phosphate buffer, pH 7.5, DPC, tris(carboxyethyl) phosphine (2% w/v), EDTA (0.1% w/v), sonication (1 min), extrusion and then, Sodium 2-mercapto-ethanesulfonate (2% w/v); (b) $Hg(OAc)_2$, 10% aq HOAc, DTT (Scheme 10).

Sequential native chemical ligation (11 or 12) is shown in Scheme 10 (FIG. 13).

Ligation between 14 and 6 to give 11: The peptide 14 (1.5 mg, 0.48 μmol) and peptide thioester 6 (0.98 mg, 0.58 μmol) was subjected to ligation reaction conditions as described in method B. The progress of the reaction was periodically monitored by MALDI-ToF and the reaction was complete within 2 hours. The crude peptide was purified by semi preparative C-4 reversed phase column using a linear gradient of 0-95% solvent B in A over a 40 min., and lyophilization of the appropriate fractions afforded 11 (1.8 mg, 85%). MALDI-ToF MS: observed, 4622.3549 Da, calculated, 4621.7785 Da.

Ligation between 14 and 8 to give 12: The peptide 14 (3.081 mg, 1 μmol) and peptide thioester 8 (1.1 mg, 1.5 μmol) was subjected to ligation reaction conditions as described in method B. The progress of the reaction was periodically monitored by MALDI-ToF and the reaction was complete within 2 hours. The crude peptide was purified by semi preparative C-8 reversed phase column using a linear gradient of 0-95% solvent B in A over a 40 min., and lyophilization of the appropriate fractions afforded 12 (2.6 mg, 73%). MALDI-ToF MS: observed, 3679.6072 Da, calculated, 3679.3928 Da.

Example II

Alternative Ligation Method

The ligation method described in Example 1 as Method B was refined to yield an alternative ligation method. The alternative method is performed, for example, at a slightly more basic pH. The alternative Method B was exemplified by the following ligation of glycopeptide 14 and lipopeptide thioester 6.

Method B (alternative). Glycopeptide 14 (1.5 mg, 0.48 μmol), lipopeptide thioester 6 (0.98 mg, 0.58 μmol), and dodecyl phosphocholine (1.5 mg, 4.4 μmol) were dissolved in a mixture of trifluoroethanol and $CHCl_3$ (1/1, v/v, 1.5 mL/1.5 mL). The solvents were removed under reduced pressure to give a peptide/lipid film on the surface of the round bottom flask. The lipid/peptide film was then dried in vacuo overnight. The ligation buffer was prepared by degassing a solution of 200 mM phosphate buffer (pH 7.5) containing tris (carboxyethyl)phosphine (2% w/v) and EDTA (0.1% w/v) in double-distilled $H_2O$ for 30 minutes and placing the solution under a strict atmosphere of argon. The pH of the degassed solution was carefully increased to 8.0 using 0.1 M NaOH. The lipid/peptide film was hydrated under a strict argon atmosphere for 4 hours at 37° C., shaking at 95 rpm, using the ligation buffer. The mixture was ultrasonicated for 5 minutes. The peptide/lipid suspension was extruded through 1.0 μm polycarbonate membranes (Whatman, Nucleopore, Track-Etch Membrane) at 50° C. to obtain uniform vesicles. To initiate the ligation reaction, sodium 2-mercaptoethane sulfonate (40 μg, 2% w/v in ligation buffer) was added to the vehicle suspension until the final concentration of peptides was 1.5 mM. The reaction was carried out in an incubator at 37° C., shaking at 95 rpm, and was complete within 2 hours. The reaction was monitored using HR-MALDI-ToF using α-cyano-hydroxycinnamic acid (prepared as 10 mg/ml in 50% aq. MeCN+0.1% TFA) as matrix. The crude reaction mixture was purified by RP-HPLC on a semi-preparative C-4 reversed phase column using a linear gradient of 0-95% solvent B in A over 40 minutes, and the fraction possessing the expected product as determined by MALDI-ToF was collected and lyophilized to give 11 (1.8 mg, 85%). HR-MALDI-ToF MS: observed, 4622.3549 Da, calculated, 4621.7785 Da.

Example III

Figure 14:
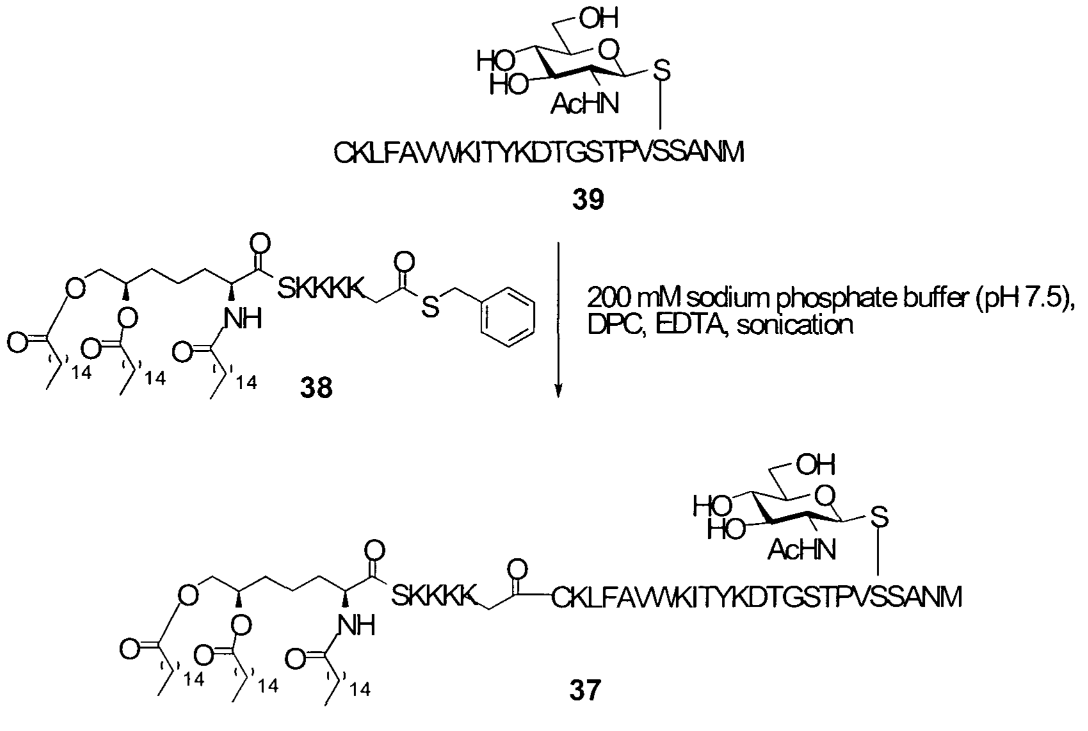
FIG. 14 shows liposome-mediated native chemical ligation of glycolipopeptide 37 from 38 and 39 in the absence of thiol initiator (Scheme 11).

Liposome-Mediated Native Chemical Ligation in the Presence or Absence of Thiol Initiator Liposome-mediated native chemical ligation between peptide thioester 38 and glycopeptide 39 having a N-terminal cysteine resulted in formation of glyco(lipo)peptide 37 (FIG. 14, Scheme 11). This reaction was carried out in the presence and absence of catalyst required for ligation reaction such as 2-mercaptoethane sulfonate or thiophenol. Surprisingly, this reaction gave similar results, indicating that the thiol initiator is not required under liposome-mediated native chemical ligation. Thus, the liposome mediated native chemical ligation can be performed in the presence or absence of thiol initiator or catalyst.

The complete disclosures of all patents, patent applications including provisional patent applications, and publications, and electronically available material (e.g., GenBank amino acid and nucleotide sequence submissions) cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

What is claimed is:

1. A method for making a multicomponent compound comprising:

mixing at least one first hydrophobic reactant comprising a carbohydrate and an N-terminal cysteine residue, at least one second hydrophobic reactant comprising a lipopeptide thioester, and a nonpolar, hydrophobic or amphipathic molecule capable of forming a lipidic structure;

subjecting the mixture to conditions effective to form a lipidic structure in which the first and second reactants are embedded; and subjecting first and second reactants to conditions effective to allow ligation of the first reactant and the second reactant to yield a multicomponent compound comprising the first and second reactant, wherein the ligation reaction takes place within the lipid phase of the lipidic structure;

wherein neither the first nor the second reactant is a transmembrane protein or membrane-spanning fragment thereof.

2. The method of claim 1 further comprising contacting the multicomponent compound with at least one third hydrophobic reactant within a lipid structure under conditions to allow ligation of the multicomponent compound and the third reactant, to yield a multicomponent compound comprising the first, second and third reactants.

3. The method of claim 2 comprising solubilizing the multicomponent compound and the third reactant within a lipidic structure to facilitate ligation of the multicomponent compound to the third reactant.

4. The method of claim 1 wherein the lipidic structure is selected from the group consisting of a lipid monolayer, lipid bilayer, a liposome, a micelle, a film, an emulsion, a matrix and a gel.

5. The method of claim 1 further comprising contacting the lipidic structure with an initiator compound to catalyze the ligation.

6. The method of claim 1 wherein the ligation is performed in the absence of an initiator compound.

7. The method claim 1 wherein the lipid structure comprises an amphipathic molecule.

8. The method of claim 1 wherein at least one reactant comprises a T-epitope.

9. The method of claim 1 wherein at least one reactant comprises a B-epitope.

10. The method of claim 9 wherein the B-epitope is from a microorganism selected from the group consisting of a virus, a bacterium, a fungus, and a protozoan.

11. The method of claim 10 wherein the microorganism is a human immunodeficiency virus or a hepatitis C virus.

12. The method of claim 9 wherein the B epitope is overexpressed on a cancer cell.

13. The method of claim 1 wherein the first hydrophobic reactant comprises a self-antigen.

14. The method of claim 13 wherein the self-antigen comprises a MUC-1 glycopeptide.

15. The method of claim 1 wherein the first hydrophobic reactant comprises a glycoconjugate selected from the group consisting of a glycosylated protein, a glycosylated peptide, a glycosylated lipid, a glycosylated amino acid, a DNA and an RNA.

16. The method of claim 1 wherein the second hydrophobic reactant comprises a lipopeptide adjuvant.

17. The method of claim 1 wherein the second hydrophobic reactant comprises a Toll-like receptor (TLR) ligand.

18. The method of claim 17 wherein the Toll-like receptor ligand comprises $Pam_3Cys$ or $Pam_3CysSK_n$, wherein n=0, 1, 2, 3, 4 or5.

19. The method of claim 1 wherein the second hydrophobic component comprises $Pam_3CysSK_4$.

20. A method for making a multicomponent compound comprising:

mixing at least one first hydrophobic reactant comprising a self-antigen and an N-terminal cysteine residue, at least one second hydrophobic reactant comprising a lipopeptide thioester comprising $Pam_3CysSK_n$ wherein n=0, 1, 2, 3, 4, or 5, and a nonpolar, hydrophobic or amphipathic molecule capable of forming a lipidic structure;

subjecting the mixture to conditions effective to form a lipidic structure in which the first and second reactants are embedded; and subjecting first and second reactants to conditions effective to allow ligation of the first reactant and the second reactant to yield a multicomponent compound comprising the first and second reactant, wherein the ligation reaction takes place within the lipidic structure;

wherein neither the first nor the second reactant is a transmembrane protein or membrane-spanning fragment thereof.

21. The method of claim 20 wherein at least one reactant comprises at least one B-epitope, at least one T-epitope, or a combination thereof.

* * * * *